US012782335B2

(12) United States Patent
Schaff et al.

(10) Patent No.: US 12,782,335 B2
(45) Date of Patent: Nov. 3, 2026

(54) DEVICES AND METHODS FOR PLASMA SEPARATION AND STORAGE

(71) Applicant: Laboratory Corporation of America Holdings, Burlington, CA (US)

(72) Inventors: Ulrich Schaff, Pleasanton, CA (US); Kyungjin Hong, Pleasanton, CA (US); Laura Fredriksen, Pleasanton, CA (US); Gabriella Iacovetti, Pleasanton, CA (US); Jon Epperson, Pleasanton, CA (US); Ali Rahimian, Pleasanton, CA (US); Greg Sommer, Pleasanton, CA (US); Sean Hong, Pleasanton, CA (US); Eric Kendall, Pleasanton, CA (US)

(73) Assignee: Laboratory Corporation of America Holdings, Burlington, NC (US)

( * ) Notice: Subject to any disclaimer, the term of this patent is extended or adjusted under 35 U.S.C. 154(b) by 1023 days.

(21) Appl. No.: 17/259,158

(22) PCT Filed: Jul. 9, 2019

(86) PCT No.: PCT/US2019/040945
§ 371 (c)(1),
(2) Date: Jan. 8, 2021

(87) PCT Pub. No.: WO2020/014190
PCT Pub. Date: Jan. 16, 2020

(65) Prior Publication Data

US 2021/0156842 A1 May 27, 2021

Related U.S. Application Data

(60) Provisional application No. 62/719,626, filed on Aug. 18, 2018, provisional application No. 62/715,213,
(Continued)

(51) Int. Cl.
*G01N 33/49* (2006.01)
*B04B 5/04* (2006.01)
*G01N 1/40* (2006.01)

(52) U.S. Cl.
CPC ......... *G01N 33/491* (2013.01); *B04B 5/0407* (2013.01); *G01N 1/4077* (2013.01)

(58) Field of Classification Search
CPC ... G01N 33/491; G01N 1/4077; B04B 5/0407
See application file for complete search history.

(56) References Cited

U.S. PATENT DOCUMENTS 4,056,225 A * 11/1977 Hein, Jr. ............... B04B 5/0428 494/24
6,455,250 B1 * 9/2002 Aguilera ................. C12N 9/22 435/456
(Continued)

FOREIGN PATENT DOCUMENTS

GB 1276730 * 6/1972
GB 1276730 A 6/1972
(Continued)

OTHER PUBLICATIONS

Stanford Environmental Health and Safety, Centrifuge Safety, https://ehs.stanford.edu/reference/centrifuge-safety, accessed Jan. 26, 2024, available Dec. 11, 2016 per internet archive. (Year: 2016).*
(Continued)

*Primary Examiner* — Jennifer Wecker
*Assistant Examiner* — Kathryn Elizabeth Limbaugh
(74) *Attorney, Agent, or Firm* — Kilpatrick Townsend & Stockton LLP

(57) ABSTRACT

A centrifugal cartridge or disk used for extraction of light supernatant fractions from fluid samples is described, particularly for non-homogenous fluid biological samples such as whole blood. The device may be used to collect cell-free
(Continued)

blood plasma or a fraction of whole blood containing target cells such as leukocytes. Single or multiple channels are described, including channels with passive valves, gaskets, receiving cavities, inlet holes, capillary wicking ridges, distal cavities for cell retention, separator gel, and density medium. Centrifugal action causes whole blood in a receiving cavity to pass into one or more channels where it separates into blood cells, plasma and optionally fractions of an intermediate density. After spin, the plasma returns to the receiving cavity by way of the one or more channels for extraction through the inlet hole or other inwardly located hole. Disposable cartridges are constructed of monolithic top and bottom plates, which may be joined together by an elastomeric outer seal.

40 Claims, 21 Drawing Sheets

Related U.S. Application Data filed on Aug. 6, 2018, provisional application No. 62/695,387, filed on Jul. 9, 2018.

(56) References Cited

U.S. PATENT DOCUMENTS

| | | | | |
|---|---|---|---|---|
| 2003/0176267 | A1* | 9/2003 | Eberle | B04B 5/0428 494/21 |
| 2008/0017577 | A1* | 1/2008 | Yi | B01L 3/502 210/645 |
| 2012/0309636 | A1* | 12/2012 | Gibbons | C12Q 1/42 435/6.12 |
| 2016/0023204 | A1* | 1/2016 | Schaff | G01N 35/04 422/533 |
| 2016/0223516 | A1 | 8/2016 | Nishijima et al. | |
| 2017/0080422 | A1* | 3/2017 | Maaskant | B01D 17/0217 |
| 2018/0126377 | A1* | 5/2018 | Horii | B01L 3/502707 |
| 2018/0353950 | A1* | 12/2018 | Maurer | G01N 21/25 |

FOREIGN PATENT DOCUMENTS

| | | | | | |
|---|---|---|---|---|---|
| JP | 5253470 | A | | 4/1977 | |
| JP | 521 45578 | A | | 12/1977 | |
| JP | H06201638 | | * | 7/1994 | |
| JP | 2000189407 | A | * | 7/2000 | B01L 3/50215 |
| JP | 2016507065 | A | | 3/2016 | |
| WO | WO-9721090 | A1 | * | 6/1997 | B01F 13/00 |
| WO | 2014124179 | A1 | | 8/2014 | |
| WO | WO-2015112768 | A1 | * | 7/2015 | B01D 21/262 |

OTHER PUBLICATIONS

English Espacenet Machine Translation of JP2000189407A. (Year: 2000).*

English Espacenet Machine Translation of JPH06201638A. (Year: 1994).*

EP19834761.9 , “Intention to Grant”, Mar. 14, 2023, 9 pages.

EP23189539.2 , “Extended European Search Report”, Nov. 23, 2023, 8 pages.

JP2021-523557 , “Notice of Decision to Grant”, Oct. 3, 2023, 3 pages.

JP2021-523557 , “Office Action”, Apr. 4, 2023, 4 pages.

* cited by examiner

Before Spin

During Spin

After Spin

Before Spin

After Spin

Before use

After separation

Section view E - E

Section view F - F

Section view G - G

Section view H - H

Before Spin

During Spin

After Spin

J - J CROSS SECTION

K - K CROSS SECTION

L - L CROSS SECTION

Section view M - M

DEVICES AND METHODS FOR PLASMA SEPARATION AND STORAGE

BACKGROUND OF THE INVENTION

This invention relates to the fluidic separation of biological samples and, in particular, relates to a device comprising a centrifugal cartridge, which separates whole blood into plasma and blood cell components, and method for its use.

Blood analysis is extensively used for various diagnostic purposes and usually requires serum or plasma sample free of red blood cells. A whole blood sample is typically collected by venipuncture through a needle, which can be attached to an evacuated collection tube to facilitate aspiration of blood from a subject such as a human patient or (in veterinary situations) an animal. Separation of the blood into serum or plasma (a lighter fraction) and red blood cell (a heavy fraction) is then accomplished by centrifugation. As analytical processing of the separated plasma or serum sample is not performed at the point of blood draw in most cases, blood is transported from the collection site to an analysis lab causing a delay between blood collection and separation and processing. However, prolonged contact with unseparated blood cells causes degradation of the serum or plasma by the continuous release of cellular contents and metabolites. Therefore, for many analytes, blood must be separated by centrifugation prior to shipment to the analysis lab.

For clinical testing, serum or plasma may be transferred into yet another container after centrifugal separation from cellular components, and such transfer operations are time-consuming and are either labor-intensive or require expensive automatic handling. Another conventional method to maintain the separation of the liquid and blood cell phases after centrifugation is to provide a sort of phase separator. Thixotropic gel such as polyester gels is the most common phase separator that can be found in many blood collection and separation tubes. Such blood collection tubes rely on the specific gravity of the gel to locate the gel at the liquid-blood cell interface, as shown in U.S. Pat. No. 4,050,451 to Colombus, and U.S. Pat. No. 3,920,549 to Gigliello. Upon subjection to centrifugal force, the gel that is initially located in the bottom of the tube moves upwardly to the liquid-blood cell interface. Although useful, it is known that the use of thixotropic gel as a separator possesses limited shelf-life as well as contributing to performance problems, such as potential cell/platelet contamination of plasma or fibrin formation in serum samples that affect downstream analysis or instrument.

For these reasons, a variety of devices to mechanically partition the fluid phases of the blood have been designed and proposed. For instance, a mechanical separator is initially affixed to the tube wall and is positioned at the phase interface by elevated gravitational forces during centrifugation, as described in U.S. Pat. No. 5,533,518 to Volger. Another example of separator movable in the interior space of the tube under centrifugation is described in U.S. Pat. No. 3,887,464. Upon centrifugation, a piston containing an internal valve that is actuated by a centrifugal force moves down through the liquid phase while retaining sealing engagement with the inner surfaces of the container. Its movement ends at a predetermined distance by positive stop means, and the internal valve automatically closes to provide an impenetrable barrier between the liquid and solid phase of blood upon the termination of centrifugation. U.S. Pat. No. 9,682,373 B2 discloses a separator body containing two or more materials with distinct densities and possessing an overall density intermediate the densities of a liquid phase and solid (blood cell) phase. Initially, the blood sample and suspended particles can pass around the separator, and following completion of centrifugation, the separator expands (and the tube contracts) preventing the fluid from passing through it.

Although such mechanical separators overcome some limitations of gel separators, there are significant drawbacks, including barrier failure under certain circumstances. Additionally, due to structural complexity, most mechanical separators are complicated and costly to manufacture requiring multi-part fabrication techniques. Furthermore, the vast majority of such mechanical separators are designed to work in conventional blood tubes, which require a centrifuge of a minimum size to operate. Increasingly, blood collection for medical and wellness testing is moving toward the end customer, such as with mobile phlebotomy services and capillary blood collection techniques such as fingerstick. Nonetheless, analytical test labs remain highly centralized to maintain efficiency and continue to require separated plasma for certain types of testing. Due to the standard size of conventional blood tubes and the necessity for the center of rotation to lie outside of the tube during centrifugation, the need to support the tube under considerable force, and the armor required to protect users from high-speed components, compatible centrifuges are necessarily too large to be readily portable. Accordingly, a need arises to develop a separator device that (i) prevents cross-contamination of plasma and blood cells during and after centrifugation, (ii) has fully functional but structurally simple barrier, (iii) can provide plasma with low cell contamination, (iv) is capable of separating blood in a reduced time frame, (v) enables separation with a centrifuge of minimal size.

SUMMARY OF THE INVENTION

A device comprising a centrifugal cartridge and a method of using the cartridge to separate a fluid suspension containing particles into a pelleted heavy fraction and a recoverable supernatant or heavy fraction is described. The device and method may be applied to the separation of whole blood into a light plasma fraction and a heavy cellular fraction. The invention may be configured to retain sub-populations of particles derived from whole blood in the plasma fraction. The device and method is primarily described in the application of separation of plasma from whole blood, but it should be understood that the device and method may be applied other fluid mixtures containing at least two fractions separable by density.

The device may comprise a hollow disk-shaped cartridge, closed at the periphery and open to a receiving cavity toward an axis of rotation nearer the center of the disk shape. Alternately, the device may comprise a hollow elongated cartridge, closed at an outer end and open to a receiving cavity and inlet hole at a proximal end, the proximal end being closer to an axis of rotation.

Cartridges may be constructed primarily from a top plate and a bottom plate attached such as by ultrasonic welding, adhesive, or over-molding. In preferred embodiments, the top plate and bottom plate are joined by a rubbery, elastic, or elastomeric material that can stretch under force and return to its original shape when force is removed.

Whole blood or sample fluid may be loaded into the receiving cavity described above through an inlet hole. The cartridge may then be placed into a centrifuge and spun. The blood may then move due to centrifugal force through one or more channels towards the periphery. Blood may then be separated by centrifugal force into a plasma fraction (supernatant or lighter fraction) toward the axis of rotation and a cellular fraction (pellet or heavier fraction) toward the periphery or outer end. The outer end or periphery of the cartridge may have one or more distal cavities sized to contain a portion of the cellular fraction or the entire cellular fraction following the end of centrifugation. In disk-shaped embodiments, the cavity sized to contain the cellular fraction may be a ring-shaped distal cavity. The plasma fraction supernatant may be returned to the receiving cavity by way of the one or more channels following the end of centrifugation.

Surface tension and capillary action on the fluid may play an important role in the maintenance of separation after the spin, especially when small volumes such as less than 1 mL of fluid are to be separated. Elastic deformation of the cartridge during centrifugation and elastic rebound following centrifugation may also play an essential role in the maintenance of separation after the spin. Channels may have deep portions and shallow portions. A shallow portion may encourage wicking through the channel via capillary action. A shallow channel portion may be implemented either as variable channel depth or variable channel width. Channels connecting the receiving cavity to peripheral cavities may expand during centrifugation by separation of the top plate and bottom plate, and contract following centrifugation by elastic rebound. Portions of the interior of the cartridge, which may include the channels, may comprise elastomers that may form a hermetic seal or gasket preventing liquid interchange between the receiving cavity and distal cavities. In this manner, the plasma fraction may be hermetically sealed from the cellular fraction.

The plasma fraction may be recovered from the receiving cavity such as by liquid aspiration through the inlet hole. The device may alternatively contain a separate chamber for plasma recovery or may comprise one or more outlet holes for extraction of plasma. Plasma may be maintained in a separated state by the cartridge following centrifugation for one or more days before the plasma is extracted, stored within the cartridge for one or more days.

The device and method may enable centrifugal systems that are more portable or compact than conventional tube-based centrifugal systems used for fluid separation. The device and method may enable separation of blood shortly after collection in facilities lacking conventional centrifugal systems and shipment of separated plasma to analytical laboratories.

DETAILED DESCRIPTION OF THE INVENTION

Figure 1A:
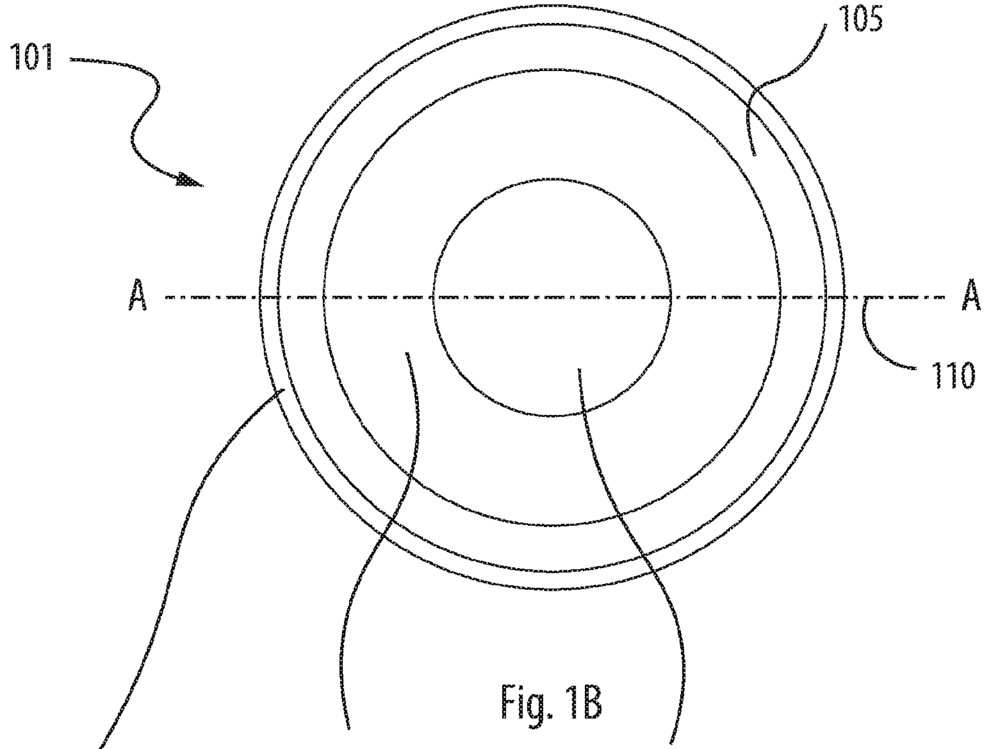
FIGS. 1A-B are a top view and cross-section of disk-shaped cartridge embodiment.

Descriptions, scenarios, examples and drawings are non-limiting embodiments. All references to "invention" refer to "embodiments." It is to be understood that alternative variations and embodiments as well as various combinations of those may be assumed and that the embodiments describe herein are simply exemplary embodiments of the invention. It is also understood that drawings are not to scale, emphasis instead being placed upon generally illustrating the various concepts discussed herein.

The device of the present invention, also called a cartridge or apparatus, is intended to be used in a centrifuge and spun about an axis of rotation. For purpose of the description hereinafter, the words "distal", "proximal", "end", "inward", "outward" and like spatial terms, if used, shall relate to an axis of rotation. A "top view" is typically looking down on the embodiment, looking into the axis of rotation. A "side view" has the axis of rotation vertical, with "inward" features nearer to the axis of rotation and "outward" features further from the axis of rotation. Likewise, "distal" and "end" features are relatively further from the axis of rotation and "proximal" and "inward" features are relatively closer to the axis of rotation.

Embodiments described herein are of a device intended for use in separation of a sample fluid into higher and lower density phase components, or into heavy (pellet) fraction and light (fluid supernatant) fraction, and methods of using the device. The device of the present invention can be used to provide a separation of plasma or serum from whole blood, and to facilitate recovery of the plasma or serum. Embodiments described herein may refer to a sample comprising whole blood, which is separated into a plasma fraction, and a cellular fraction. It should be understood that the methods and devices may be more generally applied to a sample comprising a separable mixture (corresponding to whole blood) that may be separated into a higher density heavy fraction (corresponding to the cellular fraction) and a lower density light fraction (corresponding to the plasma fraction). It should be understood in some cases that the heavy fraction may comprise packed particles such as packed blood cells following centrifugation. Packed blood cells in particular are known to occupy a specific range of percentages of the total blood volume following centrifugation.

Plasma or serum may be maintained in a separated state from the cellular fraction through differential elasticity of components of the devices, which causes a hermetic sealed area between two components of the device to open when the rotational force or centrifugation is applied to the device loaded with a sample, and to cause the hermetic sealed area to close when the rotational force or centrifugation is removed. It should be understood that hermetic sealing means that flow of liquids and gasses may be restricted or fully prevented across the sealed area.

Exemplary volume of a sample to be processed with the device described herein may be within the range of 0.1 mL to 10 mL. In alternate embodiments, the device may be used to process a sample with a volume of 10 to 30 mL. Some embodiments may be optimized for smaller volume ranges such as between 0.05 mL and 1 mL. Cartridges are rotated at an effective rate for an effective time to enable separation of the sample into the higher density fraction and 200 lower density fraction. Examples of an effective rate of rotation include rotation rate of at least 3,000 RPM, such as at least 6,000 RPM, but preferably less than 12,000 RPM. Effective rotation rates may also include ranges such as 8,000 to 12,000 RPM, which are higher than the rotation rates used for conventional blood separation. One example of an effective time range for rotation is 10 to 600 seconds. A preferred effective time range is 30 to 300 seconds. Rotation of the cartridge at an effective rate for an effective time may be following by a reduction in spin rate over a second time period. For instance, the cartridge may be rotated at 1,000-5,000 RPM for 10 to 120 seconds. This rotation at a second period may allow heavy particulates to detach from interior surfaces and produce a higher purity plasma fraction (or other light fraction).

The device of the present invention comprises a top plate and bottom plate both of which are joined to a seal around the circumference. Exemplary material for the top plate and bottom plate of the cartridge may include but not be limited to medical grade polypropylene. Additional exemplary materials are polyethylene, polystyrene, ABS, PET, PETG, PVDF, and Topas® COC polymer. The cartridge may be disk-shaped with a diameter of 2 to 15 cm, more preferably within the range of 4 to 10 cm.

The centrifuge may have a mating hub for attachment of the cartridge to a rotary motor. The centrifuge comprises an axis of rotation, typically, but not necessarily through the hub. In some embodiments the axis of rotation passes through the cartridge at an axis of rotation point. In some embodiments the cartridge may couple directly to the rotary motor of the centrifuge, as part of a device embodiment, or part of a method embodiment, or in use.

Referring now to the drawings, FIG. 1A shows a top view of a disk-shaped cartridge 101. Major elements of a cartridge, from center toward periphery, comprise a sample receiving cavity 102, a tapered region outward from the receiving cavity 103, a separation channel 104, a distal cavity 105 outward from the separation channel 104, and an outer seal 106 that secures the top plate 107 and the bottom plate 108. Indicia for section A-A is shown by line 110.

The outer seal 106 may be a separate element or may be part of the bottom plate 108 or the top plate 107, or both. That is, the function of the outer seal 106 may be realized without a separate component. The outer seal 106 may comprise adhesive, or be created by ultrasonic welding, adhesive, a solvent, press fit, or preferably, an elastomeric joint formed by over-molding. Most preferably, the outer seal 106 will be a separate element that is made from a material that is more elastic (lower elastic modulus) than the material of the top plate or bottom plate. The outer seal 106 may be fabricated from elastomeric material such as thermoplastic elastomers, silicone elastomers, polyurethane elastomers, fluoroelastomers, or butyl rubber. Elastomeric materials herein refer to materials with a viscoelastic character which may substantially extend or stretch under a force, may conform to fill small gaps under compressive force, and may return to an original configuration when force is removed. The elastomeric material may have a hardness of less than 95 Shore A durometer, and may preferably have a hardness of between 25 Shore A durometer and 70 Shore A durometer. The outer seal 106 may form a hermetic seal (i.e. seal that prevents the passage of any gas, liquid, or solid) without gaps with the top plate 107 and the bottom plate 108.

Figure 1B:
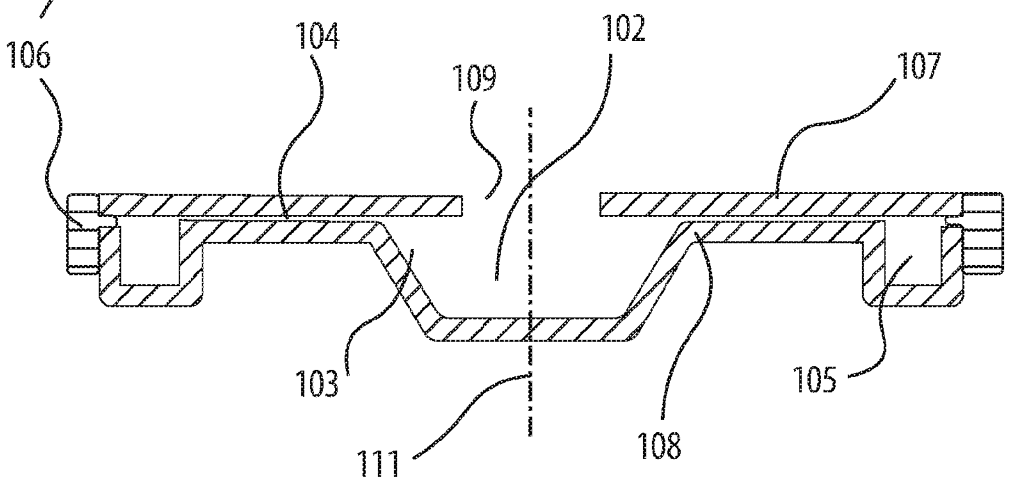

FIG. 1B shows a cross-sectional side view of the disk-shaped cartridge 101. In the embodiment shown, a recess in the bottom plate 108 forms a receiving cavity 102 with a bottom inner surface on the bottom plate 108 and a flat top inner surface on the top plate 107, and opens at an inlet hole 109 of the top plate. In other embodiments the receiving cavity, also called an entry cavity or entry chamber, may be formed from a recess in the top plate only, or a combined recess in the top and bottom plates. In one embodiment shown in FIG. 1B, the sample receiving cavity may be centered on an axis of rotation 111. In this embodiment, the axis of rotation 111 is perpendicular to a plane between the top plate 107 and the bottom plate 108. In other embodiments, the sample receiving cavity may contain the axis of rotation or may surround the axis of rotation such as by being an annular cavity around the axis of rotation. The inlet hole 109 is located in fluid communication with the receiving cavity 102 and is positioned, in the embodiment shown, such that a means for fluid withdrawal can access the receiving cavity 102. Outward from the receiving cavity 102, there is a tapered region 103 in fluid communication with the receiving cavity and with a tapering angle between 15° to 85° with respect to a plane perpendicular to the axis of rotation. Preferably, the tapering angle will be between 20° and 75°. In the example shown in FIG. 1B, the tapering angle is solely implemented in the bottom plate, but it is possible to implement a tapering angle in both the bottom plate and top plate or solely in the top plate. The combined volume of the receiving cavity 102 and the tapered region 103 will be greater than or equal to the volume of the sample fluid to be received, such as a blood sample.

Remaining in reference to FIG. 1B, outward from the tapered region 103 is a separation channel 104 formed by the top plate 107 and bottom plate 108. In the embodiment shown, the separation channel is an annular channel that is joined with the tapered region 103 extends circumferentially around the tapered region 103 with a fixed height between its top surface and bottom interior surface. The height of the separation channel 104 may be equal to or less than 0.5 mm when the cartridge is at rest. As explained later, the height of the separation channel 104 may increase when the cartridge contains a liquid and is rotated at an effective rate. More preferably, the height of the separation channel 104 may be less than 0.1 mm when the disk is at rest. In some embodiments, the separation channel may have no measurable height (that is a height equal to 0) when the cartridge is at rest. The radial length of the separation channel 104 may be 1⁄10 to ½ of the total radius of the cartridge 101. More preferably, the width of the annular separation channel 104 may be ⅕ to ⅓ of the radius of the cartridge 101. The upper and lower surfaces of the separation channel 104 may be substantially flat and perpendicular to the axis of rotation as shown. The separation channel 104 may be optionally sloped downwards from a plane perpendicular to the axis of rotation such as by 1-45 degrees from the distal end of the separation channel back to the proximal receiving cavity 102, to facilitate gravitational flow of separated fluid supernatant such as plasma back into the receiving cavity 102, assisted by capillary wicking action. Connected to the distal end of separation channel 104 is a distal cavity 105, also called a cell collection groove. In the embodiment shown in FIG. 1, the distal cavity is ring-shaped, extending within the circumference of the cartridge. Other embodiments may have multiple distal cavities distributed around the periphery of the cartridge. The height of the distal cavity 105 may be greater than the minimum height within the separation channel 104. The height of the distal cavity may be less than or equal to the height of the receiving cavity. The volume of the distal cavity 105 should be greater than the volume occupied by the heavy fraction of the sample fluid following centrifugation, and less than the volume of the entire sample fluid. For example, the volume of the distal cavity 105 may be 50%-60% of the expected volume of blood which a cartridge is configured to separate. For embodiments intended for blood separation, the volume of the distal cavity 105 will be between 30-60% of the combined volume of the receiving cavity 102 and tapered region 103. The width of the distal cavity 105 may be 1⁄15 to ⅕ of the radius of the disk-shaped cartridge 101. More preferably the width of the distal cavity 105 may be 1⁄10 to ⅕ of the radius of the disk-shaped cartridge 101. It is desired that the volume of distal cavity 105 be equal to or larger than the packed volume of blood cells.

In can be seen that the cartridge 101 has an interior comprising the sample receiving cavity 102, tapered region 103, separation channel 104, and distal cavity 105. Surfaces of the preceding features are interior surfaces. The interior of the cartridge is linked to the exterior by the inlet hole.

Figure 2A:
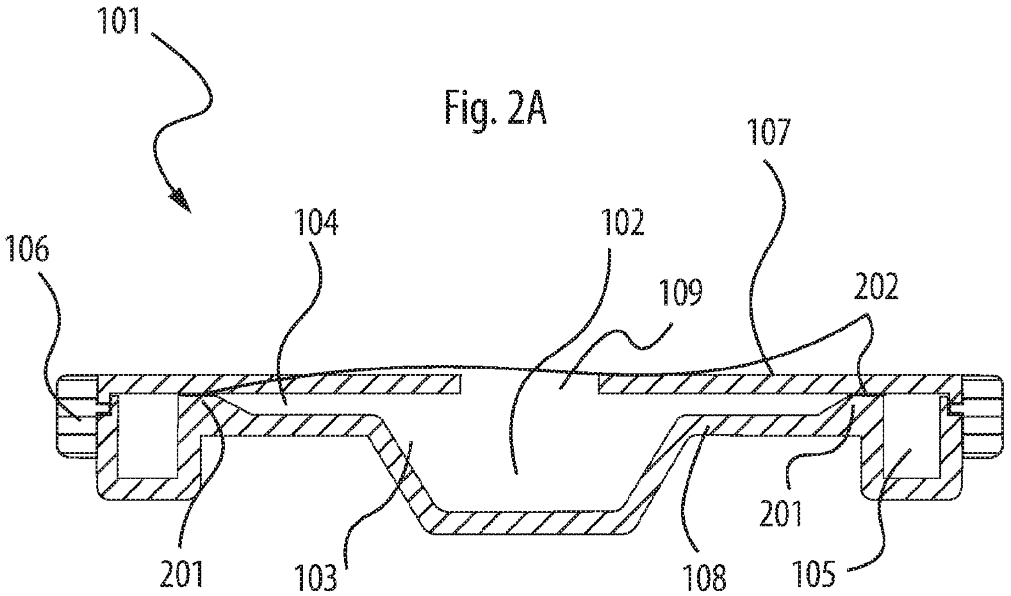
FIGS. 2A-C illustrate cross-sections of more embodiments of cartridge with projections within separation channel.
Figure 2B:
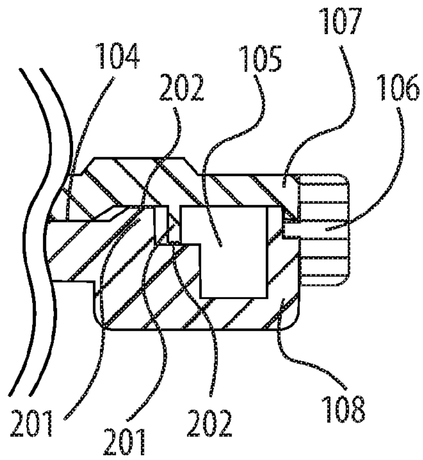
Figure 2C:
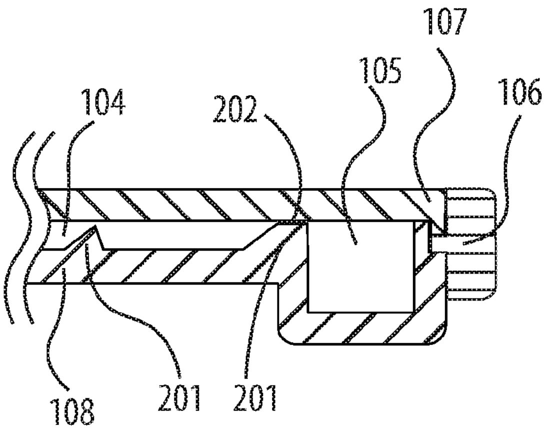

Turning now to FIGS. 2A, 2B and 2C, embodiments further comprise at least one projection 201, which may extend from the top or bottom surface of the separation channel 104. In the embodiments shown, the projections 201 are annular projections extending around the cartridge without interruption, but projections extending part way around are possible. One or more annular projection 201 create one or more contact points 202 in between the bottom plate 108 and the top plate 107 when the cartridge 101 is at rest. It should be understood that the top plate and bottom plate may come into contact (e.g. have 0 distance) at the contact points or a narrow channel such as less than 0.05 mm may exist between the top part and bottom part at the contact points 202. Contact points 202 may act to prevent fluid transmission between the distal cavity 105 and the tapered region 103 as shown in FIG. 2A. The projection 201 may comprise an extension of either one or both of top plate 107 and bottom plate 108 toward the opposite plate. The annular projection 201 may be made of the same material as the top plate 107 and the bottom plate 108. The projection 201 may form a contact point 202 prior to spin that may open when the cartridge rotated at an effective rate while containing a sample fluid to provide a passage for the sample and sedimenting particles to the distal cavity 105, and may close again after centrifugation to provide a barrier (i.e. contact point 202) between the supernatant fraction and pellet fraction of the sample.

Turning to FIG. 2A, a cross-sectional side view of a disk-shaped embodiment is shown with one annular projection 201 from the bottom plate 108 at the distal end of the separation channel 104. One annular contact point 202 is shown between the top plate 107 and the bottom plate 108, separating the tapered region 103 from the distal cavity 105. In this example and in following examples, a projection 201 has a sloped surface facing the axis of rotation toward the center of the cartridge. This sloped surface may facilitate movement of particles such as blood cells into the distal cavity 105 during rotation without particles sticking to the surface. The surface may be sloped 1-45 degrees with respect to a plane perpendicular to the axis of rotation.

FIGS. 2B and 2C show detailed cross-section side views of embodiments comprising alternative configurations of projections 201.

Turning to FIG. 2B, an alternate embodiment detail of the distal end of one side of a disk-shaped embodiment is shown. In this example, one annular projection 201 extends from the bottom plate 108 and another annular projection 201 extends from the top plate 107, forming two contact points 202 near the distal end of the separation channel 104. The proximal surface of the inner annular projection 201 may be sloped while the proximal surface of the outer annular projection 201 may be vertical.

Turning to FIG. 2C, two annular projections 201 are shown extending from the bottom plate 108. The two projections have greater distance from each other than the two projections shown in FIG. 2B. In alternate embodiments, the separation channel may comprise more than two projections. In alternate embodiments projections may extend from the top plate or from both the top plate and bottom plate. Multiple projections have the advantage of providing redundant and more effective sealing between the distal cavity and more proximal cavities following separation of blood into plasma and cellular fractions. Each contact point 202 may have different opening pressure, such that for instance, the more proximal contact point may open at the initial phase of centrifugation (i.e. lower centrifugation speeds) followed by opening of the distal annular projection at the higher centrifugation speeds.

Figure 3A:
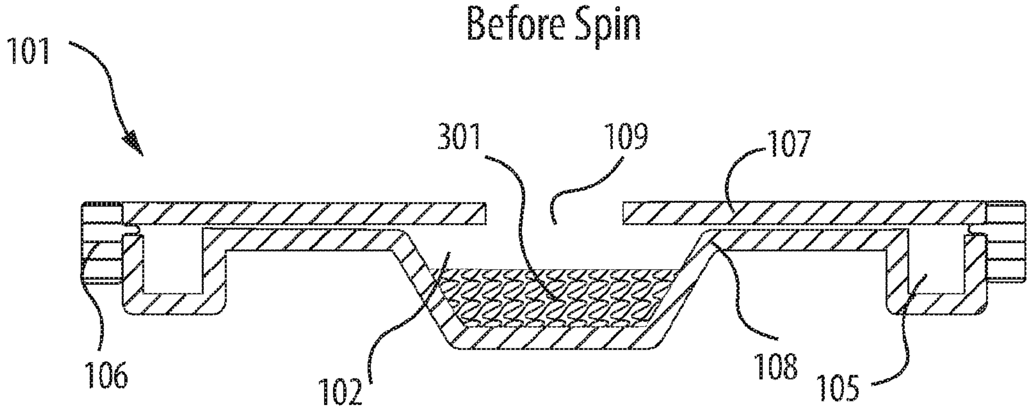
FIGS. 3A-C illustrate the embodiment of FIGS. 1A-B, containing a sample fluid before, during, and after a rotational spin.
Figure 3B:
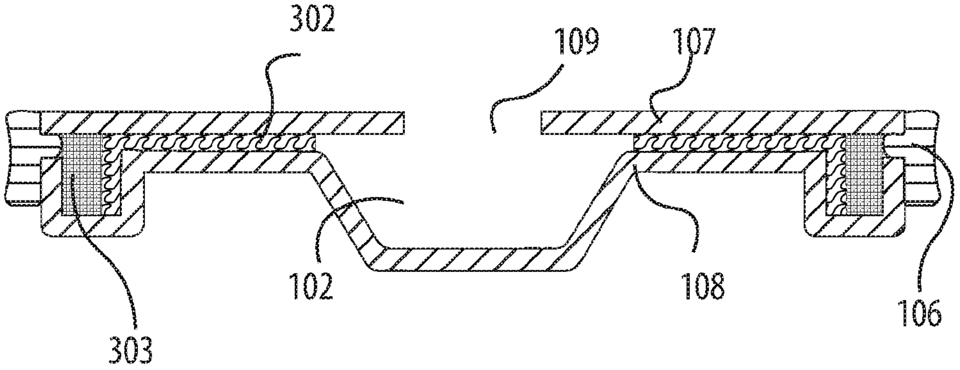
Figure 3C:
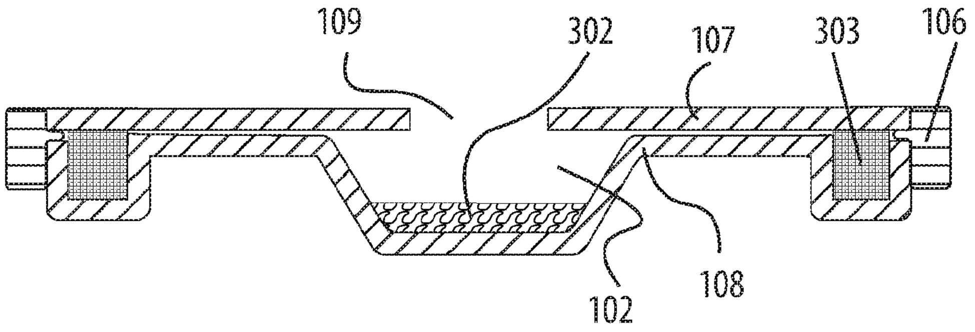

The working mechanism of the cartridge 101 of FIG. 1 is illustrated in FIG. 3A through 3C. The working mechanism shown in FIG. 3A through 3C is generally applicable to other embodiments described herein.

FIG. 3A shows an embodiment of the cartridge 101 loaded with whole blood 301 (or other sample fluid) prior to centrifugation. The cartridge 101 may include an additive such as an anticoagulant, preferably in the sample receiving cavity 102, such that loaded whole blood or sample fluid 301 contacts the anticoagulant promptly after sample loading. Anticoagulants may include but are not limited to salts of heparin, salts of ethylene diamine tetraacetic acid (EDTA), or sodium citrate. The whole blood or sample fluid 301 may remain in the sample receiving cavity 102 and the tapered region 103 before spin. During the rotational spin, the whole blood 301 may first be moved by centrifugal force into the tapered region. Whole blood may not initially be able to enter the separation channel 104, causing a build-up of pressure due to centrifugal force on the fluid. This pressure may cause the material of the outer seal 106 to deform and stretch, causing the distance between the top plate 107 and bottom plate 108 within the separation channel 104 to increase as shown in FIG. 3B. This increase in distance and resulting enlargement of the separation channel height allows whole blood or sample fluid 301 to pass into the separation channel 104 and distal cavity 105. Upon centrifugation, the distance between at least one portion of the top surface and the bottom surface of the separation channel 104 may increase by more than 50%. The increased volume of the separation channel 104 may enable the entire sample fluid 301 to enter the separation channel and distal cavity 105 as shown in FIG. 3B. Distal migration of fluid due to elastic deformation of the outer seal 106 may increase the efficiency of separation by (i) increasing the effective centrifugal force due to increased distance from the axis of rotation, (ii) decreasing the distance which cells must migrate for separation, and (iii) moving fluid into a region where the surfaces are parallel to the effect of centrifugal force and therefore less susceptible to surface adhesion. Centrifugal force generated by spinning at an effective spin rate then separates the plasma 302 (lighter fraction) from the cellular fraction 303 (heavier fraction), as shown in FIG. 3B. The heavier cellular fraction 303 will be driven outward to form a pellet within the distal cavity 105 while the plasma fraction 302 will float on the cellular fraction 303 in more inwardly located regions of the cartridge.

Turning to FIG. 3C, after centrifugation the outer seal 106 may rebound to its original state and the separation channel 104 may return to its original dimensions. FIG. 3C shows separation and entrapment of the heavier cellular fraction 303 in the distal cavity 105. Most of the lighter plasma fraction 302 is expelled into inward portions of the cartridge such as the sample receiving cavity 102 and tapered region 103 by the elastic rebound of the cartridge. In some embodiments, the resting state of the separation channel 104 will be complete closure, and all plasma contained within the separation channel 104 will be expelled inward. In some embodiments, plasma may then be recovered through the inlet hole for further use or processing.

Figure 4:
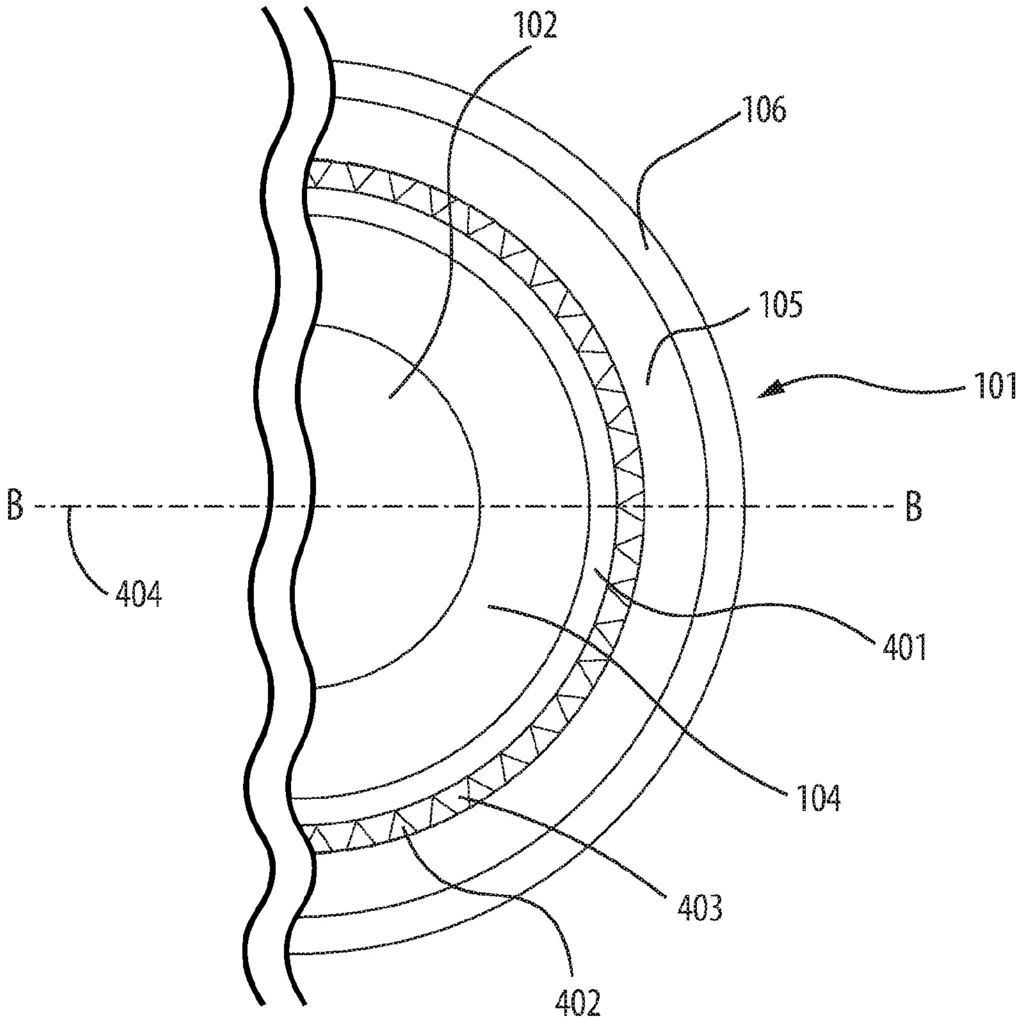
FIG. 4 illustrates a top view of a disk-shaped cartridge comprising O-ring and an array of posts and passages.

Turning now to FIG. 4, a portion of a top view of an embodiment of a disk-shaped cartridge 101 is shown, which comprises an O-ring 401 radially inward from a distal cavity 105 and radially outward from an annular separation channel 104. Indicia for section B-B is shown by line 404. The O-ring 401 may be made of an elastomeric material such as silicone rubber, fluoroelastomer, or other rubber material. The O-ring 401 may have an outer diameter of 2 cm-8 cm and a thickness of 1.5 mm-5 mm while uncompressed. The hardness of the O-ring 401 may be equal to or less than Shore durometer 60 A, more preferably, be within the range of 30 A to 50 A. A series of passages 403 and posts 402 may be located outward from the O-ring 401 and inward from the distal cavity 105. As described later, the O-ring 401 is located between the top plate and bottom plate (not shown) and may form a hermetic seal between the sample receiving cavity 102 and the distal cavity 105 while the cartridge 101 is at rest. When the cartridge is rotated while containing a sample fluid, pressure may cause the top plate and bottom plate to separate as described earlier in connection with FIG. 3B, allowing fluid and particles to pass the O-ring. The posts 402 are shown presenting a non-flat surface toward the O-ring 401 such that all the posts 403 direct impinging particles toward the distal cavity 105 during centrifugation, while fluid and particles may pass around through the passages 403. The passages 403 comprise spaces between the posts 402 with a depth greater than the posts 402. The posts 402 and passages 403 may alternately comprise a continuous variation in height of the space between the O-ring 401 and the cell capture groove 105. The purpose of the passages 403 and posts 402 is to retain the O-ring 401 in position while permitting fluid passage as the elastomeric material of the O-ring expands outward during centrifugation. In another embodiment, the O-ring 401 may position toward the inner edge of the separation channel 104 where it meets the sample receiving cavity 102, in which case the posts 402 and passages 403 would lie between the O-ring 401 and the main body of the separation channel 104. Alternately, the O-ring may lie within the middle of the separation channel 104, bisecting it into two sections.

Figure 5A:
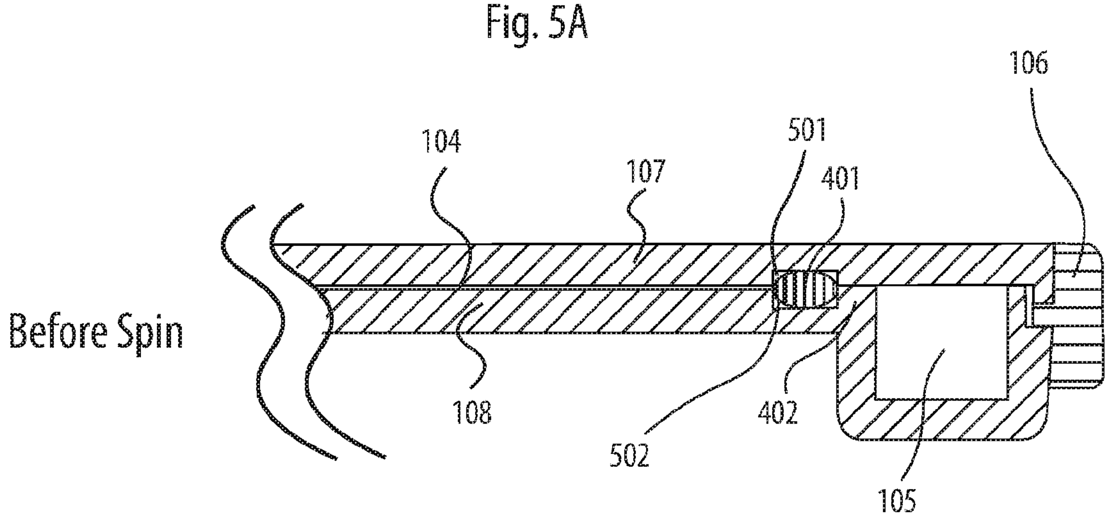
FIGS. 5A-B show a cross-section details toward the periphery of the embodiment of FIG. 4 before and after a rotational spin.

FIG. 5A shows cross-section B-B of the embodiment of FIG. 4 at rest before a rotational spin. In one embodiment, the O-ring 401 may be contained in a top groove 501 located in the top plate 107 and a bottom groove 502 located in the bottom plate 108. The top groove 501 and bottom groove 502 holding the O-ring 401 are shown to be rectangular, but may also be rounded to substantially match the profile of the O-ring 401. Prior to centrifugation, the O-ring 401 may be compressed between the top plate 107 and bottom plate 108, forming a hermetic seal between the receiving cavity 102 and the distal cavity 105. The maximum surface distance between the top groove 501 and bottom groove 502 may be less than the uncompressed thickness of the O-ring 401. The separation channel 104 may be fully closed (i.e. have a height of 0) before the spin or may have a height of less than 0.5 mm. The posts 402 and passages 403 (not shown in this cross-section) are shown in the bottom plate, but may also be located within the top plate 107. The posts 402 may be part of both top plate 107 and bottom plate 108 of cartridge 101. Posts 402 on the bottom plate 108 may contact the corresponding surface of top plate 107 when the cartridge is at rest. In an alternate embodiment, posts 402 on the top plate 107 may contact the surface of the bottom plate 108. In an alternate embodiment, there may be a gap between the posts 402 and the opposite parts before the spin.

Figure 5B:
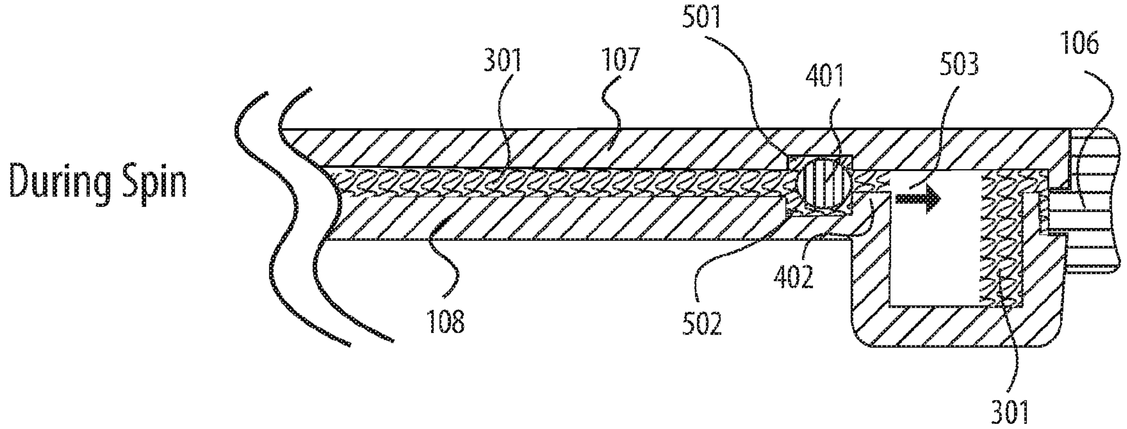

FIG. 5B shows a distal portion of a cross-section B-B of the embodiment of FIG. 4 during a rotational spin at an effective rate while containing a sample fluid 301. In this embodiment, the elastic outer seal 106 may expand due to rotational force or fluid pressure or both, increasing the distance between the top plate 107 and bottom plate 108. The minimum distance between the top surface of the posts 402 and the opposite surface on the other plate (in this example the top plate 107) during the centrifugation must be less than the thickness of the O-ring 401. During the spin, the posts 402 may hold the O-ring 401 and prevent formation of a seal and may allow fluid flow through the passages 403. A sample fluid such as whole blood may therefore flow around the O-ring 401 into the cell capture groove 105 in the outer direction 503. During the spin, sedimenting particles may pass around the O-ring 401 and through the open passages 403 into the distal cavity 105 forming a pellet in the distal cavity similar to that shown in FIG. 3B. After the rotational spin is completed and the cartridge is again at rest, the top plate 107, bottom plate 108, and O-ring 401 structure may return to the rest configuration as shown in FIG. 5A. The O-ring 401 may again compress between the top plate 107 and bottom plate 108, which may result in formation of a hermetic seal between the distal cavity 105 and the separation channel 104 and fluid or particles contained in each cavity. For example, a cellular fraction (not shown) may be contained in the distal cavity 105 while the majority of a plasma fraction (not shown) may be expelled to inward cavities.

Figure 6A:
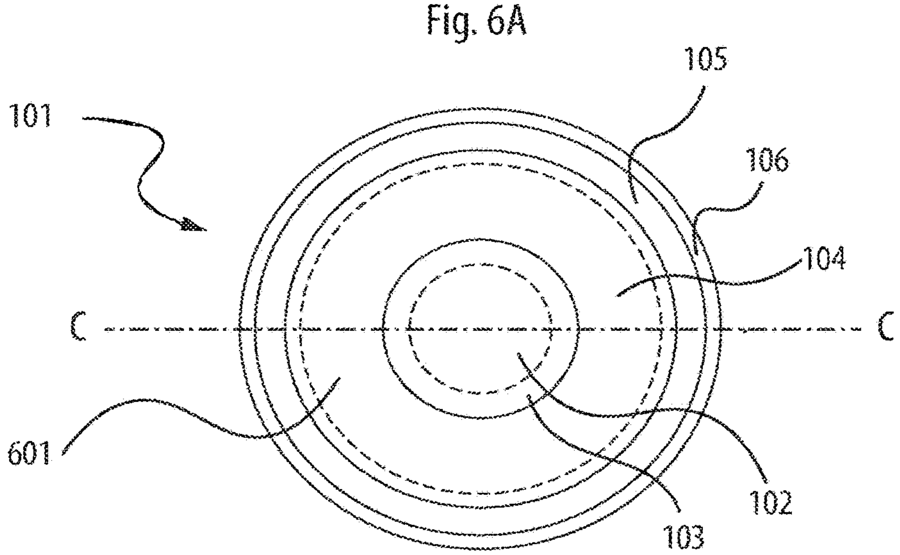
FIGS. 6A-E show a top view, cross-section view, and cross-section details of alternate disk-shaped cartridge embodiments with an elastomeric gasket.

Turning now to FIG. 6A, the cartridge 101 may consist of a gasket 601 partly located within the separation channel 104. Such gasket 601 may be an elastomeric gasket made of the same type of elastomeric materials that comprises the outer seal 106 as described earlier in association with FIG. 1A. The gasket 601 may be fabricated from identical material as the outer seal 106 or from a different elastomeric material. Such gasket 601 is shown positioned primarily in the annular separation channel 104, with a portion extending in a portion of the distal cavity 105 such that the boundary 609 is located in the distal cavity 105. Indicia for section C-C is shown by line 610.

Figure 6B:
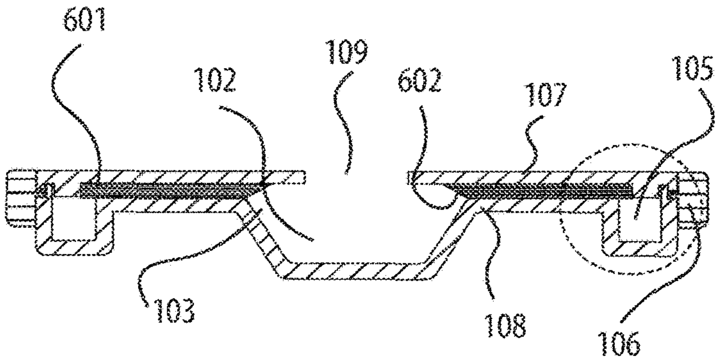

FIG. 6B shows a cross-section side view of the embodiment of FIG. 6A. In FIG. 6B, a gasket 601 is shown attached to the top plate 107 and a proximal surface of gasket 602 is shown to taper within the tapered region 103. The tapering angle for surface of gasket 602 may be between 15° to 85° with respect to a plane perpendicular to the axis of rotation. Preferably, the tapering angle will be between 20° and 75°. The gasket 601 is shown to also contact the bottom plate 108 within the separation channel 104 such that the separation channel is closed when the cartridge is at rest as shown. If the cartridge is rotated at an effective rate while containing a sample fluid, the separation channel may expand due to stretching of the outer seal enabling fluid to pass from the sample receiving cavity 102 to the distal cavity 105 as described earlier in connection with FIG. 2. After a cartridge containing a sample fluid completes rotation at an effective rate for an effective time and ceases to rotate, a cellular fraction may be retained in the distal cavity 105 while the majority of a plasma fraction may be expelled inward into the tapered region 103 and the sample receiving cavity 102. The gasket 601 is shown attached to the top plate 107 but may alternately be bonded to the bottom plate 108 with tapering in the opposite direction. In alternate embodiments, two or more elastomeric gaskets may be implemented together such as one gasket attached to the top plate and one gasket attached to the bottom plate. Such gaskets may contact each other to form a hermetic seal.

Figure 6C:
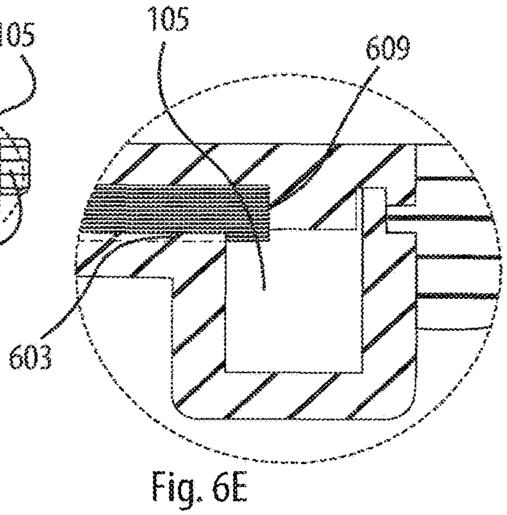

Turning to FIG. 6C, a detail of the cross-section of FIG. 6B is shown. The gasket 601 is shown to be compressed within the separation channel 104 by a compression depth 603, forming a hermetic seal between the sample receiving cavity 102 and the distal cavity 105 shown in FIG. 6B. The depth of compression of gasket 601 may be 10-1000 microns. In the embodiment shown, the distal cavity 105 is bounded by surfaces from the bottom plate 108, top plate 107, and gasket 601. It should be understood that elastomeric materials may fill small imperfections such as small recesses in the opposite surface when under compression due to the material's viscoelastic nature, enabling a robust hermetic seal. It is preferable that such gasket 601 be applied to either top plate 107 or bottom plate 108 during an irreversible process such as over-molding or adhesive to form a hermetic seal against passage of gasses or liquids between top plate 107 and bottom plate 108 of the cartridge 101 while at rest. The hermetic seal may be broken when the cartridge is rotated at an effective rate while containing a sample fluid as described, and a hermetic seal may be re-established when the cartridge ceases to rotate.

Figure 6D:
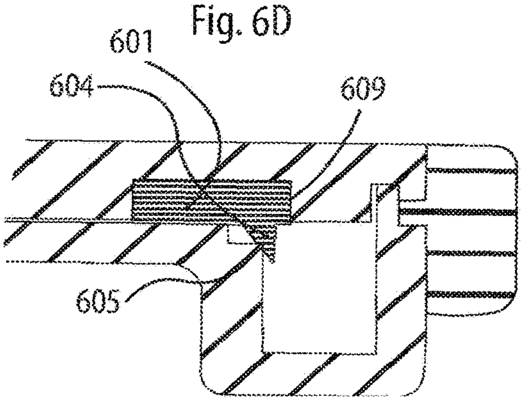
Figure 6E:
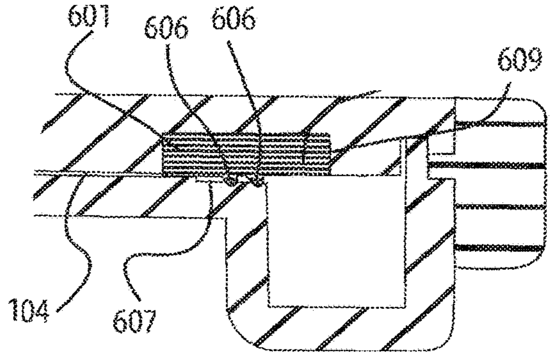

FIGS. 6D and 6E, followed by FIG. 7A through 7D show cross-sectional detail views of alternate embodiments, toward the periphery of a disk-shaped cartridge 101 including gasket 601. In these embodiments, instead of filling the whole separation channel 104, the gasket 601 is shown to overlay only a portion of the top plate 107. In such embodiments, the height of the separation channel 104 that is not covered by the gasket 601 may be zero while the cartridge is at rest, or the height may be a different value such as less than 0.5 mm or less than 0.1 mm. It should be understood that the embodiments of FIGS. 6D, 6E, and 7A through 7D may be combined with a gasket that extends through the separation channel as shown in FIG. 6A through 6C. It should be understood that the embodiments of FIGS. 6D, 6E, and 7A through 7D may alternately fuse gasket features to the bottom plate instead of to the top plate as shown.

Turning to FIG. 6D, the gasket 601 is shown to further comprise an elastomeric valve 604. Such elastomeric valve 604 may be designed to be actuated by centrifugal force or pressure from a sample fluid or both and may open only in one direction such as outward from the receiving cavity 102 and toward the distal cavity 105. As an example, the elastomeric valve 604 may deflect outward when the cartridge is rotated at an effective rate due to the viscoelastic nature of the elastomeric material from which it is fabricated. In the embodiment shown the elastomeric valve 604 presents a proximal sloped surface to the inward cavities within the cartridge. As discussed elsewhere, a sloped surface enables impinging particles to deflect toward distal cavities during centrifugation rather than being retained on the surface. In the embodiment shown, the bottom plate 108 comprises an impinging surface 605 positioned between the separation channel 104 and the distal cavity 105. The impinging surface 605 may be presented by an inner corner in the bottom plate 108 as shown. The elastomeric valve 604 is shown to have a small spatial overlap with the bottom plate 108, which is meant to represent that the valve is under compression. A distal surface of the valve 604 is substantially vertical as shown. The distal surface may alternately be concave. A concave or substantially vertical distal surface has the advantage that fluid pressure in the distal cavity may strengthen the compressive seal following the end of a spin while the cartridge contains a sample.

FIG. 6E shows another embodiment, where the gasket 601 comprises multiple elastomeric valves 606 and is bonded to the top plate 107. The bottom plate 108 may possess a recess 607 located between the separation channel 104 and the distal cavity 105. The elastomeric valves 606 shown here have rounded surfaces. Here, hermetic seals may be formed where such elastomeric valves 606 interact with the surface of the recess 607 in the bottom plate 108 of the cartridge 101. It should be understood that the gasket 601 may alternately be bonded to the bottom plate 108 and the recess 607 may be situated on the top plate 107. The valves 606 are shown to have a small spatial overlap with the bottom plate 108, which is meant to represent that the valves are under compression while the cartridge is at rest.

Figure 7A:
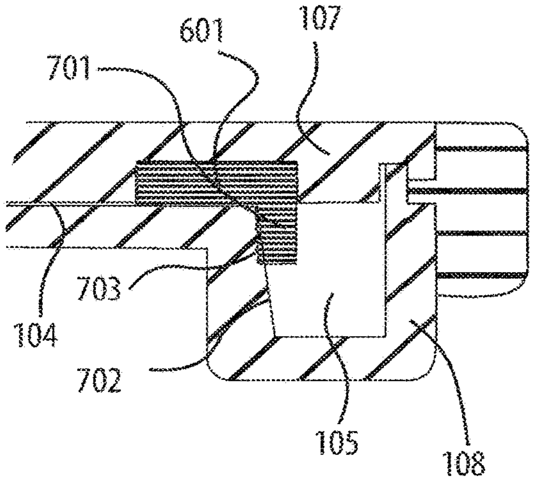
FIGS. 7A-D show alternate embodiment details from the periphery of the embodiment of FIGS. 6A-E.

Turning now to FIG. 7A the distal cavity 105 may have a slanted surface 702 on the bottom plate 108 of cartridge 101 such that the flap 701 of the elastic gasket 601 may interfere with the slanted surface 702. The flap 701 of the elastic gasket 601 may be straight or sloped with an angle of 0 to 45 degrees with respect to vertical. Preferably, the absolute value of slope of the slanted surface 702 will be greater than the value of the slope of the flap 701 when uncompressed. A hermetic seal may form at the interface of the flap 701 and the slanted surface 702. This is represented by an overlapping region indicated by 703. Due to compression of its elastomeric material, the flap 702 may actually adopt the same slope as the slanted surface 702 when the cartridge is at rest.

Figure 7B:
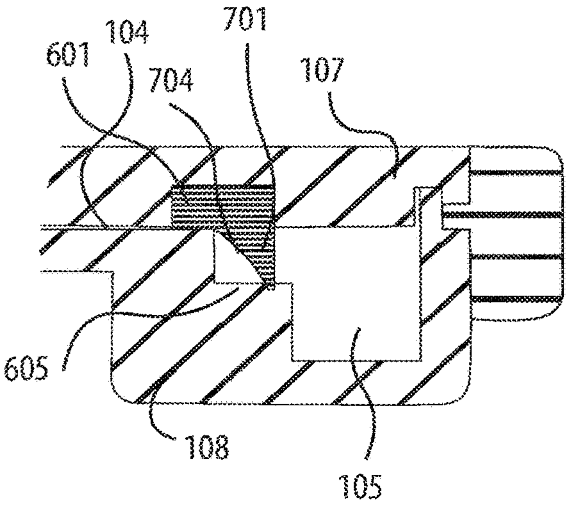

Turning now to FIG. 7B, the distal cavity 105 comprises a recess 605 to harbor a flap 701 on the bottom plate 108 of the cartridge 101. The flap 701 of the elastic gasket 601 may comprise a proximal sloped surface 704 and a distal surface, which is substantially vertical as shown or concave. The flap 701 contacts the opposite plate at impinging surface 605 where it may form a hermetic seal before and after spinning at an effective rate as described elsewhere with the effect of maintaining separation between a cellular fraction and a plasma fraction. The flap 701 may open by centrifugal forces or pressure when the cartridge is rotated at an effective rate and contains sample as described elsewhere. Preferably, the tip of flap 701 impinges against the surface 605 as shown. In general, an angle of less than 60 degrees with respect to a plane perpendicular to the axis of rotation for inward-facing surfaces on flaps, valves, or surfaces of the separating channel may be sufficient slope or taper to deflect cells into the distal cavity.

Figure 7C:
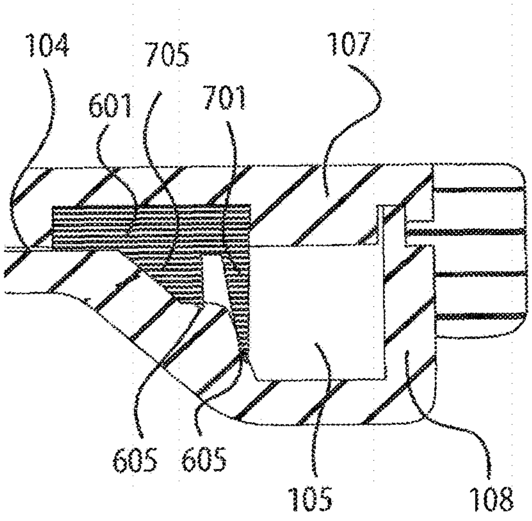

Turning now to FIG. 7C, the elastic gasket 601 comprises a tapered flap 705 and a long and flap 701 as shown prior to a rotational spin while the cartridge is at rest. In this embodiment, the surface on the proximal sector of the flap recess 605 on the bottom plate 108 of cartridge 101 is designed to be parallel to the tapered surface of the flap 705. The tip of the tapered flap 705, or the tip of the flap 701, or both may compress against impinging surfaces 605 in order to provide multiple sealing points between the annular separation channels 104 and the distal cavity 105 when the cartridge 101 is at rest.

Figure 7D:
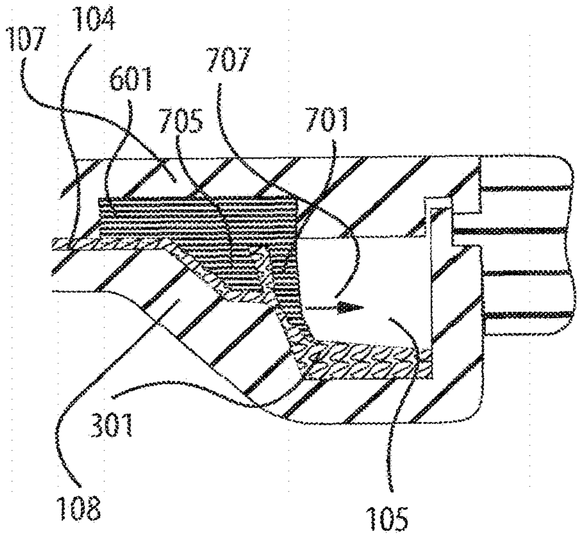

FIG. 7D shows the embodiment of FIG. 7C during a rotational spin, while the cartridge contains a sample fluid 301. Upon centrifugation, both of the flap 705 and the flap 701 of the elastic gasket 601 may be deflected radially outward in the direction 707 due to the action of centrifugal force on the viscoelastic material allowing the sample fluid 301 to pass through the gasket 601 and enter the distal cavity 105 of the cartridge 101. This mechanism of action, in which an extension of the gasket is deflected by centrifugal force, is generally also applicable to the embodiments described in association with FIGS. 6D, 6E, 7A, and 7B. Such centrifugal deflection has the advantage that the sample fluid such as a blood sample is not subjected to excessive shear stresses, reducing potential damage to particles contained in the sample. In the case of blood, such shear stress can lead to bursting of red blood cells (hemolysis).

Figure 8A:
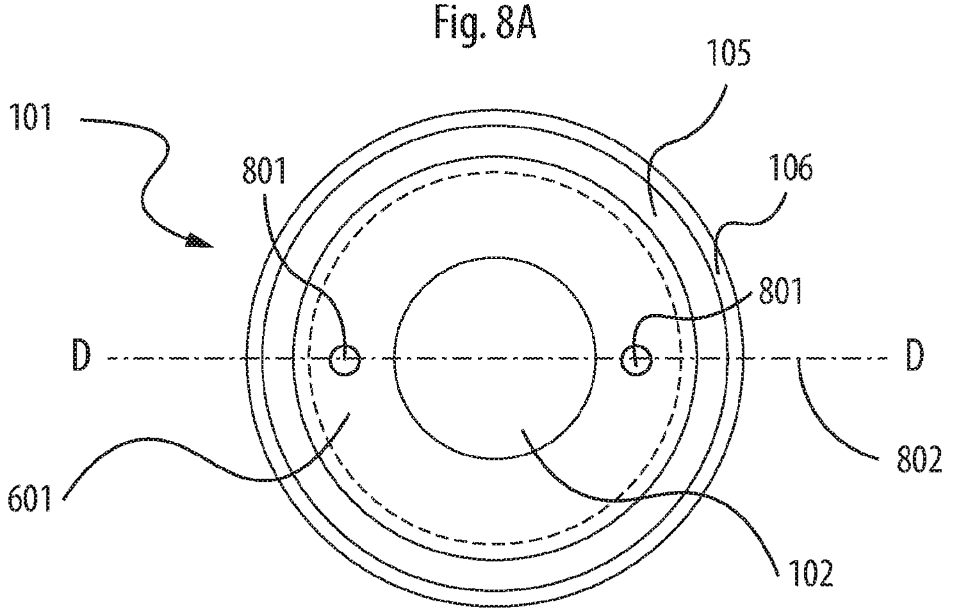
FIGS. 8A-C show a top view and cross-sectional views before and after use of a disk-shaped cartridge with an elastomeric gasket and shims.

FIG. 8A shows an alternative embodiment, comprising multiple internal spacers, also called shims 801, between the top plate 107 and the bottom plate 108 of the cartridge 101. The shims are not bonded to any surface, but may be held in place by compression of a gasket 601 while the cartridge is at rest. The outer seal 106 may be fabricated by overmolding of an elastomer under compressive force, causing residual compressive forces. Exemplary material for the shims 801 may include but are not limited to rigid plastics or metals such as stainless steel. The diameter of shim 801 may be less than or equal to the width of the distal cavity 105. The thickness of shim 801 may be 0.025-0.2 mm. Such embodiment comprises at least one shims. It is ideal to have two or more shims to be radially symmetric. The shim 801 may be located anywhere in the separation channel 104.

Figure 8B:
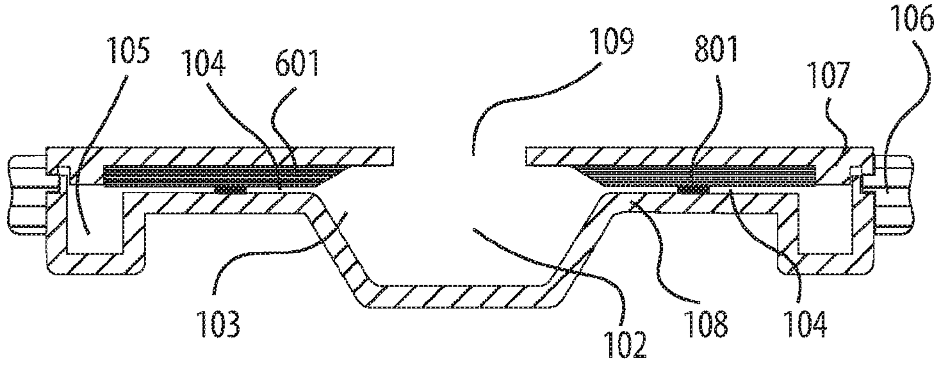

FIG. 8B shows a cross-section side view of the embodiment of FIG. 8A before placement of a sample fluid in the cartridge and at rest. Indicia for section D-D is shown by line 802 in FIG. 8A. The embodiment comprises a gasket 601 and two shims 801 located within the separation channel 104, prior to centrifugation. Shim 801 may cause partial or complete opening of separation channel 104. In the configuration shown in FIG. 8B, sample fluid (not shown) may move through the separation channel 103 and around the shims upon rotation of the cartridge at an effective rate. The sample fluid may enter the distal cavity 105 and separation channel 104 similar to the configuration shown in FIG. 3B. The presence of shims 801 may enable passage of fluid past the gasket 601 with minimal shear stress. Fluid pressure during centrifugation may cause the separation channel 104 to widen as described elsewhere. This may enable the shims 801 to escape the separation channel 104 and enter the distal cavity 105.

Figure 8C:
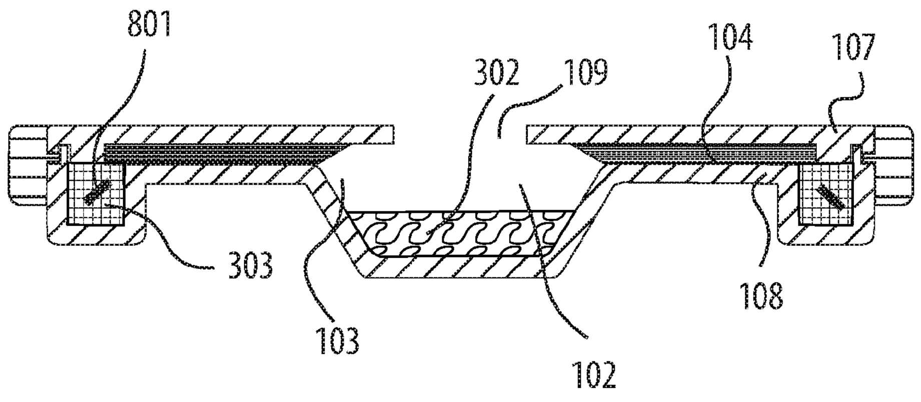

FIG. 8C shows a cross-section side view of the embodiment of FIG. 8A, after centrifugal separation of whole blood into a lighter plasma fraction 302 and heavier cellular fraction 303 and after the cartridge comes to a rest. The shims 801 which may have a diameter smaller than, or equal to the width of the distal cavity 105 are shown to have moved outward into the distal cavity 105 during the spin as described above. With the shims removed from the separation channel 103, the outer seal 106 may contract to close the separation channel forming a hermetic seal between the distal cavity 105 and interior cavities.

FIGS. 9 and 10 show alternate embodiments comprising various configurations of the separation channel 104 within a cartridge 101 further comprising connecting channels 901 and routing channels 902. Herein, connecting channel 901 and routing channel 902 both refer to a groove with greater depth than the distance between top and bottom surfaces within the rest of the separation channel 104. In some embodiments, the distance between top and bottom surfaces within the separation channel will be zero except within connecting channels 901 or routing channels 902.

Figure 9A:
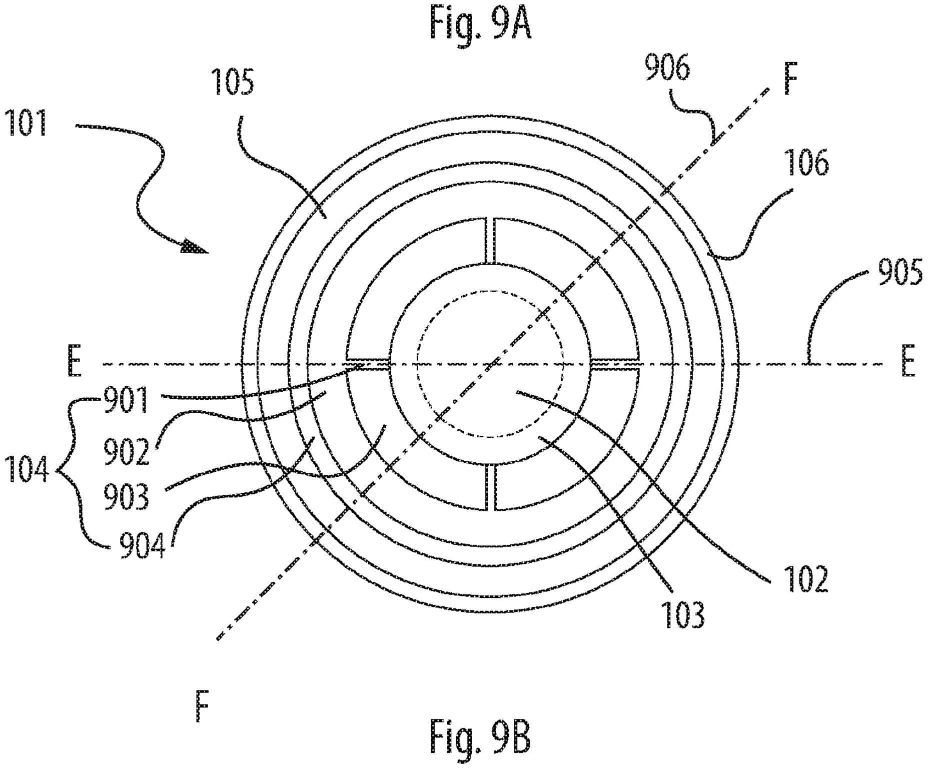
FIGS. 9A-C show a top view and cross-sectional views of a disk-shaped cartridge with an elastomeric gasket, a routing channel and multiple connection channels.

Turning to FIG. 9A, a top view of an embodiment of a cartridge 101 is shown. Four connecting channels 901 are shown, which link the sample receiving cavity to a routing channel 902. In alternate embodiments, a connecting channel may link the tapered region to the distal cavity. This alternate embodiment would prevent formation of a hermetic seal between the tapered region and distal cavity, with the advantage that sample fluid can readily travel from the receiving cavity to the distal cavity. The routing channel 902 is shown as an annular groove within the separation channel 104. Non-annular shapes for the routing channel such as line segments or partial annular sections are possible. A portion of the separation channel inward from the routing channel 902 is labeled as an inner contact 903. A portion of the separation channel outward from the routing channel 902 and inward from the distal cavity 105 is labeled as an outer contact 904. Connecting channels 901 are shown as radially symmetric, embodiments with asymmetric distribution of connecting channels are possible. Alternate embodiments may have a range of 1 to 24 connecting channels. Cross section indicators for subsequent figures are labeled as 905 for section E-E cutting through connecting channels 901 and as 906 for section F-F cutting through inner contacts 903.

Figure 9B:
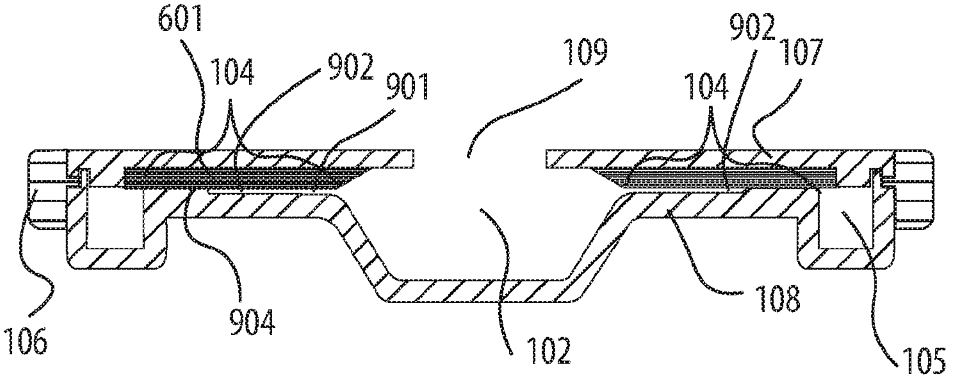

Turning to FIG. 9B, a cross-sectional side view E-E of the embodiment of FIG. 9A is shown. Connecting channels 901 are shown to have a depth equal to the routing channel 902. Routing channels may alternately have a different depth than the routing channel. Connecting channels and routing channels may have a depth of 0.01 mm to 0.5 mm. Preferably, connecting channels and routing channels may have a depth of 0.025 mm to 0.2 mm. The embodiment shown further comprises an elastomeric gasket 601 similar to those described in association with FIG. 6. Some embodiments may lack an elastomeric gasket. In some embodiments, connecting channels or routing channels may be grooves in the elastomeric gasket 601 rather than directly in the top plate or bottom plate. The outer contact 904 may form a hermetic seal between the routing channel 902 and the distal cavity 105. The distal surface of the routing channel 902 may be sloped as shown to facilitate deflection of particles into the distal cavity during centrifugation as discussed elsewhere.

Figure 9C:
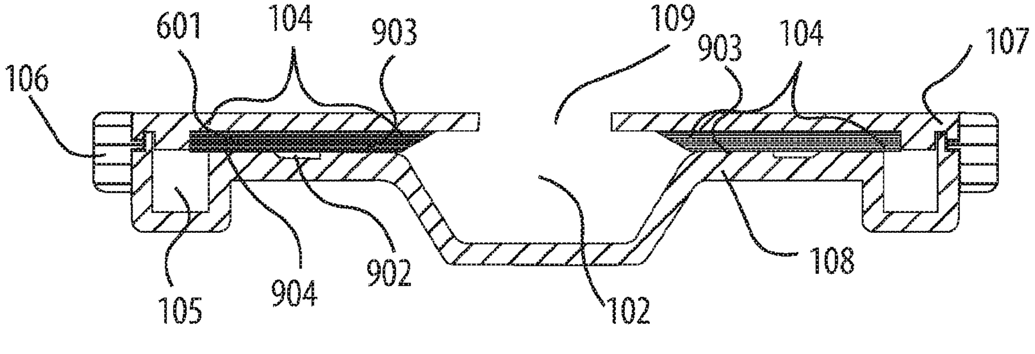

Turning to FIG. 9C, a cross-sectional side view F-F of the embodiment of FIG. 9A is shown. The elastomeric gasket 601 may be compressed at both or either of the outer contact 904 and inner contact 903. In some alternate embodiments, a small gap such as less than 0.1 mm may exist between the top plate and bottom plate at both or either of the outer contact and inner contact 903. If the cartridge is rotated at an effective rate while containing a sample fluid, the sample may first enter the connecting channels 901 and routing channels 902. Centrifugal force will cause increased fluid pressure within the connecting channels 901 and routing channels 902 which will facilitate opening of the separation channel 104 and particularly the inner seal 903 and outer seal 904. An embodiment with at least one routing channel has an advantage that fluid pressure will be exerted over a larger surface area, increasing the opening force within the cartridge. Therefore, fluid pressure required for opening the separation channel 104 will be reduced. Following completion of a rotation at an effective rate for an effective time, any compressive force exerted by the outer seal 106 will be focused on the outer contact 904 and inner contact 903, helping to re-establish a hermetic seal at the outer contact 904. Alternative embodiments may have more than one routing channel 902 such as 2 to 6 routing channels. Alternative embodiments may have routing channels only or connecting channels only.

Figure 10A:
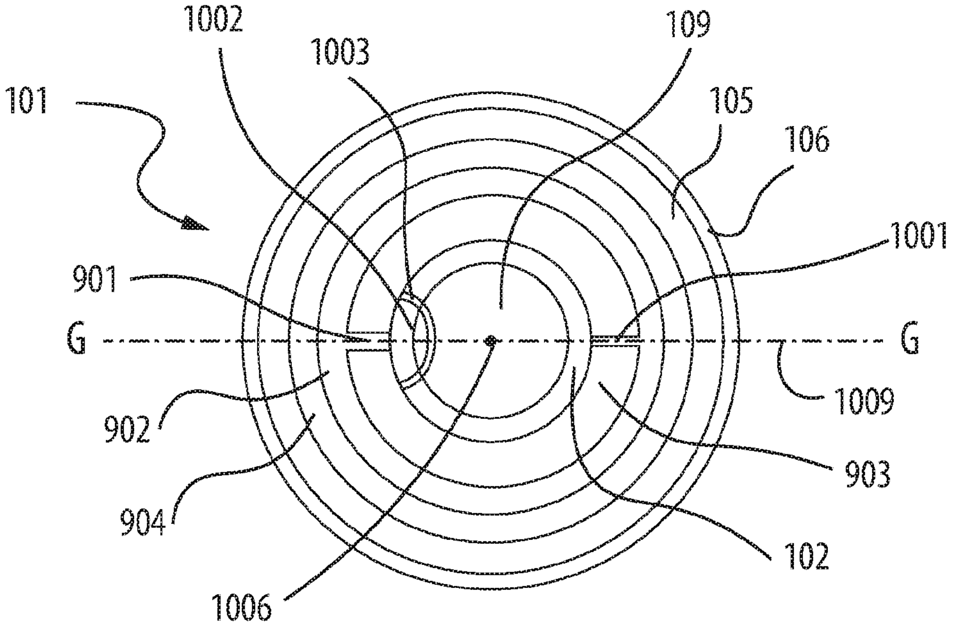
FIGS. 10A-B show a top view and cross-sectional details of a disk-shaped cartridge embodiment with an elastomeric gasket, a routing channel, a connection channel, a plasma collection cavity, and a vent channel.

Turning now to FIG. 10A, a top view of an embodiment comprising a connection channel 901 and a vent channel 1001 is shown. Both connection channel 901 and vent channel 1001 are shown to link the sample receiving cavity 102 to a routing channel 902. When the cartridge 101 is at rest, a sample fluid may move into the routing channel 902 through the connection channel 901. The vent channel 1001 may function as a means to assist the routing channel 902 become fully filled with a sample fluid by providing a passage for air. The vent channel 1001 may be smaller in width than the connecting channel 901 as shown. The embodiment shown further comprises a plasma collection cavity 1002 which may be bounded by rim wall 1003. The plasma collection cavity 1002 may be accessible from the inlet hole 109 in the top plate 107. An axis of rotation 1006 may be at the center of the cartridge 101. The plasma collection cavity 1002, may be closer to the axis of rotation 1006 than the inner seal 903. Such plasma collection cavity 1002 may have the advantage that plasma may be collected from a predictable location. After separation, the separated plasma may flow into the plasma collection cavity 1002 with assistance of capillary wicking action through the routing channel 902 and connecting channels 901.

Figure 10B:
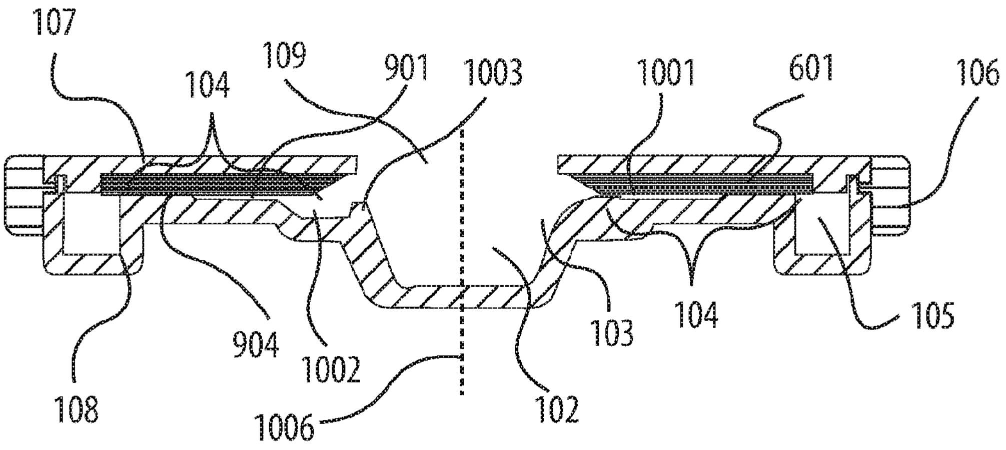

FIG. 10B shows a G-G cross-section of the embodiment of FIG. 10A and as indicated by line 1009. The distal surface of the plasma collection cavity 1002 may be sloped as shown to facilitate deflection of cells into the distal cavity 105 during centrifugation as discussed elsewhere. The depth of plasma collection cavity 1002 may be equal to, or greater than the depth of separation channel 104. The depth of the plasma collection cavity 1002 may be less than the depth of the receiving cavity 102. The volume of the plasma collection cavity 1002 may be equal to or greater than the expected volume of separated plasma following use of the cartridge. For instance, the plasma collection cavity 1002 may have a volume between 40% and 100% of the distal cavity 105.

Figure 11:
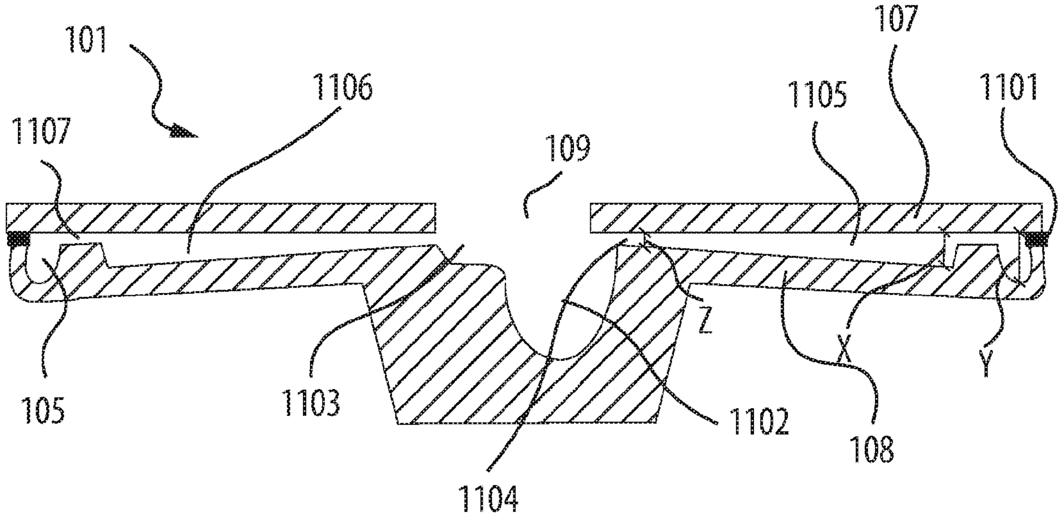
FIG. 11 shows an alternate embodiment cross-section with a shallow and deep portion of the sample receiving cavity and a channel valve.

Turning now to FIG. 11, a cross-section of an embodiment 101 of a disk-shaped cartridge 101 is shown. The embodiment may comprise at least one tapered separation channel 1106. The channel may comprise a passive entry valve 1104 and a main channel 1105, which may comprise a tapered thickness from its proximal end to its distal end such that the proximal portion is thinner than the distal end as shown in FIG. 11. The embodiment comprises a distal passive valve 1107, and a distal cavity 105. In one embodiment, the height or thickness Z at the passive valve 1104 may be less than the height or thickness of channel 1105 at its largest value X, which in turn is less than height or thickness Y of the distal cavity 105. That is: $Z<X<Y$. An asymmetric entry cavity is shown in FIG. 11, with a deeper portion 1102 and a shallower portion 1103. Additionally, the inlet hole 109 may also be asymmetric with respect to the axis of rotation of the cartridge or asymmetric with respect to the sample receiving cavity 102. In an embodiment, the wicking ridge 1103 as shown in FIG. 11, may be a height variance in the base of sample receiving cavity 102 to enable a sample fluid loading while preserving air venting. Additionally, the wicking ridge 1103 may form a base for an inlet hole, or a collection area for lighter portion of the sample fluid or blood plasma after the spin. The blood plasma may flow into the wicking ridge 1103 by capillary action. Plasma may flow onto wicking ridge 1103 by capillary action in part due to the tapered thickness of 1105 and/or 1106 described earlier. As in other embodiments, the cartridge may be joined at the exterior by an outer seal 1101.

Figure 12A:
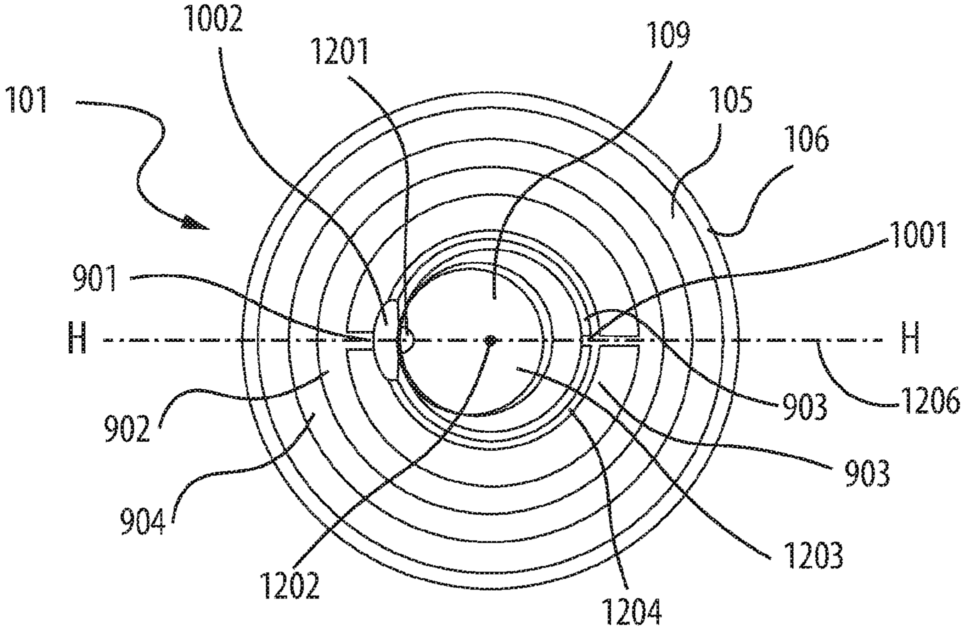
FIGS. 12A-B show a top view and cross-section view of a disk-shaped cartridge with a gasket elastomer, multiple routing channels, connection and vent channel, and access area for plasma collection.

Turning now to FIG. 12A, we show a top view of another embodiment, which comprises a connecting channel 901, a vent channel 1001, a plasma collection cavity 1002, a routing channel 902 and an inner routing channel 1204. Indicia for section H-HD is shown by line 1206 in FIG. 12A. One set of inner contacts 903 are shown between the routing channel 904 and the inner routing channel 1204, and another set of inner contacts 904 are shown inward from the inner routing channel 1204. The cartridge embodiments shown may be asymmetric, and the axis of rotation 1202 may not be at the center of the inlet hole or the center of the sample receiving cavity 102. Although the overall structure of the cartridge including the sample receiving cavity 102 may not be symmetric, the centroid of the cartridge 101 is situated at the axis of rotation 1202. The plasma collection cavity may be located outward from some inner contacts and within the annular bound of the separation channel 104. A plasma recovery point 1201 may be accessible from the inlet hole 1203.

Figure 12B:
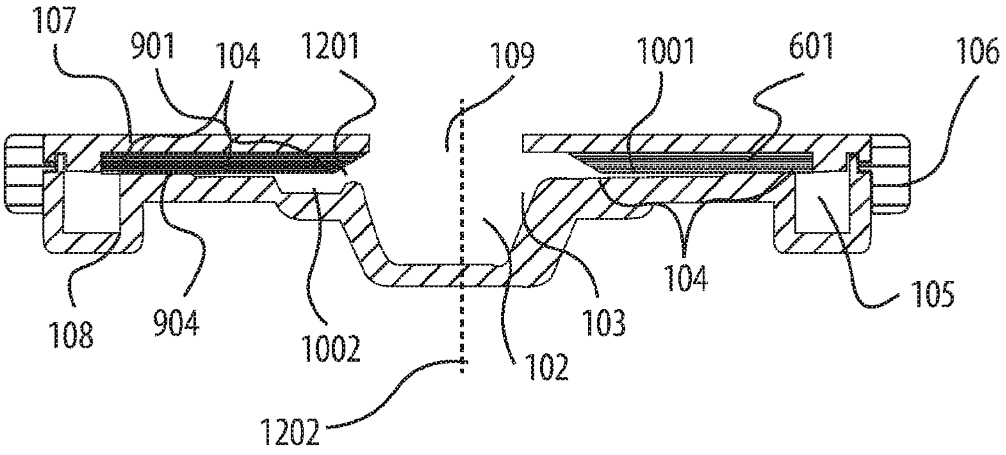

FIG. 12B shows a cross-section side view H-H of the embodiment of FIG. 12A. The plasma recovery point 1201 may be a narrow cavity in fluid communication with the plasma collection cavity 1002, located radially inward from the plasma collection cavity 1002. As described in connection with FIG. 10, plasma may flow into the plasma collection cavity 1002 through the routing channel 902, connecting channel 902 and inner routing channel 1204 following centrifugal separation of a blood sample in the cartridge 101. The outer contact 904 may serve to provide a hermetic seal between the distal cavity 105 and routing channel 902 when the cartridge is at rest as described in connection with FIG. 9. The location of the plasma collection cavity 1002 within the bound of the separation channel 104 may serve to enhance recovery of a plasma fraction within the plasma collection cavity by making accumulation of the plasma fraction in this location favorable during relaxation of the outer seal 106 following centrifugation.

Figure 13A:
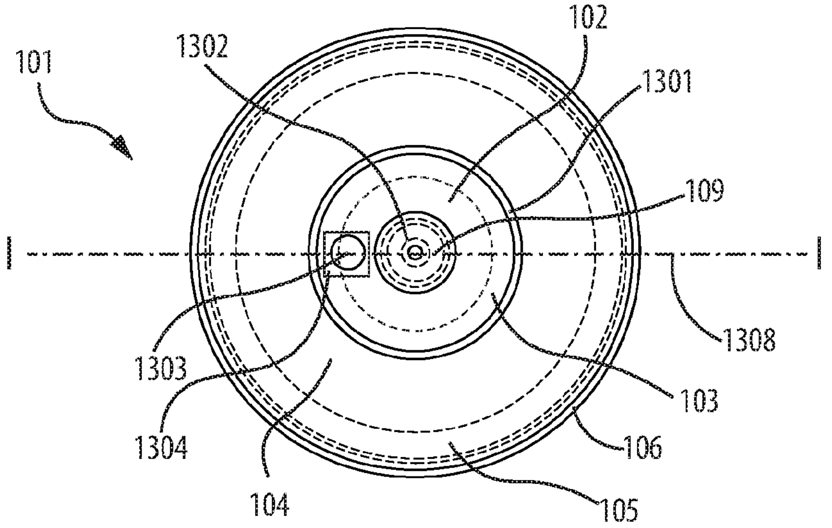
FIGS. 13A-B show a top view and cross-sectional view of a disk-shaped cartridge comprising a mating feature for a motor, a stopper in the inlet hole and an outlet hole for plasma collection.

FIG. 13A shows a top view of a disk-shaped cartridge 101 comprising a recess in the top plate 1301, an inlet hole 109 and an elastomeric stopper 1302 located within the inlet hole 109. A sample receiving cavity 102 may be formed from a combined recess in both the top plate 107 and bottom plate 108. A tapered region may be formed from tapers on both the top and bottom plates. FIG. 13A shows a top view of the cartridge 101. The stopper 1302 may comprise an elastomeric material such as rubber configured to provide a gas-tight seal that may reseal when punctured. The stopper may be combined with any of the preceding or subsequent embodiments of the cartridge. The cartridge may further comprise an outlet hole 1303 and a foil seal 1304 placed over the outlet hole, to allow extraction of lighter portion of sample fluid (i.e. blood plasma) by means for fluid withdrawal. The outlet hole 1303 may be positioned at the periphery of the sample receiving cavity 102 as shown. Alternately, the outlet hole 1303 may be positioned in the tapered region 103. The foil seal 1304 may comprise a laminated aluminum foil, a laminated glass layer, or plastic layer and may provide a hermetic gas and fluid barrier. The foil seal 1304 may comprise pressure sensitive adhesive or thermal adhesive.

Figure 13B:
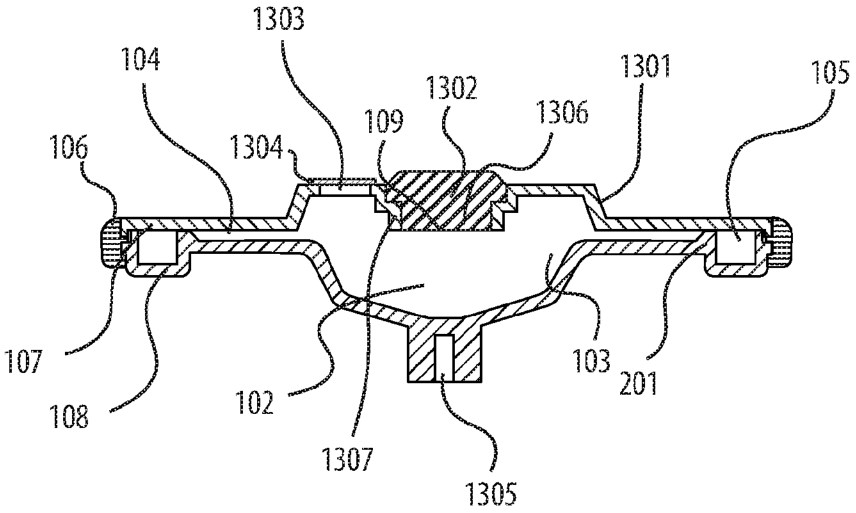

Turning to FIG. 13B, a side view cross-section of the embodiment of FIG. 13A is shown and as indicated by line 1308 in FIG. 13A. The cartridge may further comprise one or more projections 201 in the separation channel 104 such that it forms a hermetic seal between the sample receiving cavity 102 and the distal cavity 105 when the cartridge is at rest. Alternatively, the cartridge may comprise an O-ring, one or more gaskets, or other means of providing a hermetic seal as described previously. The cartridge may further comprise a hub 1305 configured to mate with a motor shaft of a centrifuge.

In the embodiment of FIG. 13, the elastic stopper 1302 may provide the capability to collect sample fluid with an evacuated cartridge. For instance, the interior of the cartridge, including but not limited to the sample receiving cavity 102, the tapered region 103, the separation channel 104, and the distal cavity 105 may be partially evacuated of air during manufacture. The evacuated cartridge may contain gasses at a pressure less than atmospheric pressure. Such evacuated containers are known to the art. Evacuation of the cartridge may facilitate, for example blood collection, by connecting sample collection device such as a butterfly needle to a patient and a second needle connected with tubing to the butterfly needle through the stopper 1302. Blood would then be aspirated from the patient into the cartridge by differential pressure through the stopper 1302. The stopper 1302 may include a plug 1306, which may be adapted to press fit into an extension of the inlet hole 1307 of the cartridge without any gaps. Such stopper may be adapted for removable mounting in the cartridge 101 while provide a hermetic seal where the plug 1306 of the stopper 1306 be in contact with the extension of the inlet hole. Alternatively, the stopper may be permanently adhered to the inlet hole 109 of the cartridge 101 such as by a solvent, adhesive, thermal bonding, or an injection overmolding process. The stopper 1302 of the evacuated cartridge may be puncturable by a fluid transfer needle allowing fluid communication with the reduced pressure interior of the cartridge so that a sample fluid is collected in the cartridge from the needle. A fluid transfer needle may be removed and the stopper 1302 may seal the cartridge 101 again. The cartridge 101 may comprise multiple layers to hold the gasses at a pressure less than atmospheric pressure (i.e. vacuum) for a prolonged time period. The cartridge 101 may contain additives. The interior or exterior surfaces of elastic stopper 1302 may be also coated with additives. The additives may include but not limited to anticoagulants, stabilizers, and surfactants. The cartridge 101 may contain anticoagulants. Anticoagulants may include but not limited to heparin, ethylene diamine tetraacetic acid (EDTA), or sodium citrate. The cartridge 101 may contain stabilizers, also known as preservatives. A preservative may include but not limited to substances configured to reduce the breakdown of nucleic acid polymers such as DNA, substances configured to reduce or prevent the breakdown of cell membranes, and substances configured to reduce or arrest the cell metabolism. Preservatives may include the anticoagulents listed above. The cartridge 101 may contain a cocktail comprising various combinations of aforementioned additives.

The cartridge of the embodiment shown in FIG. 13 may be stored in a gas-impermeable pouch such as a pouch partly comprising aluminum and evacuated by means such as a nozzle vacuum sealer or vacuum chamber sealer. After centrifugal separation of blood by such a cartridge, plasma may be extracted by puncture of the foil seal 1304 and aspiration from the sample receiving cavity 102 or from the tapered region 103.

Figure 14A:
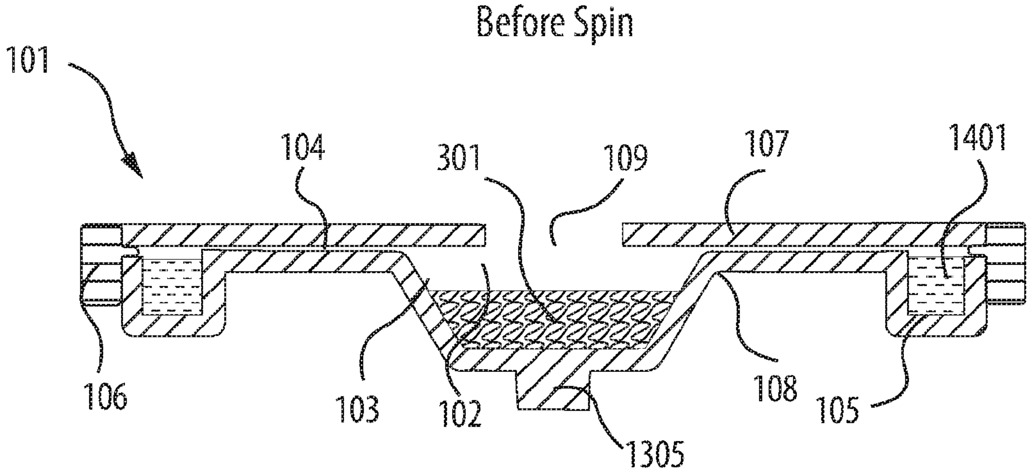
FIGS. 14A-C show the disk-shaped cartridge containing a sample fluid and combined with separator gel before, during, and after a rotational spin.

Turning now to FIG. 14A, a cross-section side view of an embodiment of disk-shaped cartridge 101 is shown that may contain a separator gel 1401 prior to a rotational spin but after input of a sample fluid 301 such as a blood sample. The details of this embodiment are otherwise similar to that described in association with FIG. 1 and FIG. 3. The separator gel 1401 initially be within the distal cavity 105 of the embodiment as shown. The separator gel 1401 may alternately be stored in any of the interior locations within the cartridge such as in the sample receiving cavity 102. The separator gel 1401 may have a density greater than a lighter plasma fraction and less than a heavier cellular fraction. For the example of blood, the separator gel may have a density of 1.03 g/cc to 1.08 g/cc. The separator gel may be a thixotropic gel, with viscosity lower than typically used for maintaining blood separation in tubes. A lower viscosity is advantageous because the gel will be maintained in cavities of smaller dimension than tubes. The volume of the separator gel 1401 may be equal to or less than the volume of the separation channel 104. Alternately, the volume of the separator gel may be between 20% and 50% of the volume of the distal cavity.

Figure 14B:
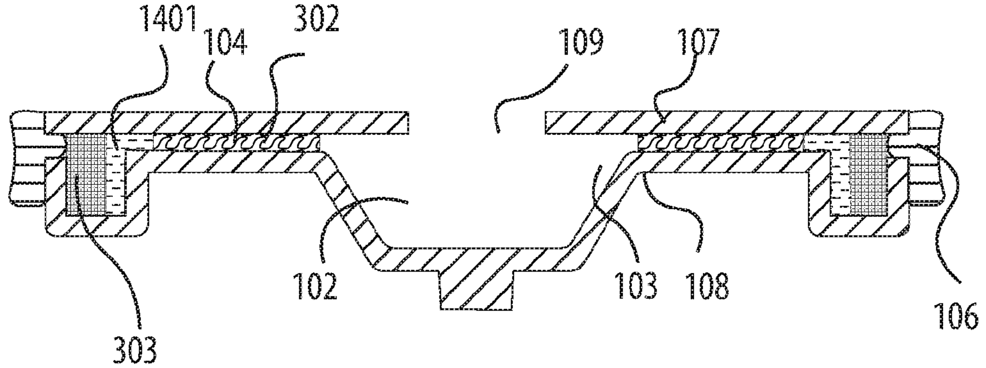

FIG. 14B shows the embodiment of FIG. 14A during a rotational spin where the whole blood or sample fluid 301 has separated into a cellular fraction 303 and a plasma fraction 302, with separator gel 1401 forming a layer between the cellular fraction 303 and plasma fraction 302. Due to stretching of the outer seal 106, the separated blood components and separator gel are within the separation channel 104 and distal cavity 105 in this state.

Figure 14C:
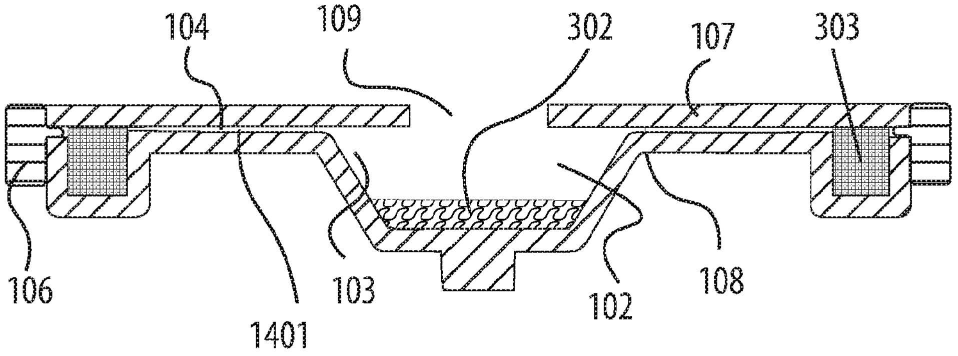

FIG. 14C shows the embodiment of FIG. 14A after a rotational spin at an effective rate is completed and the cartridge has returned to rest. As described previously, elastic rebound of the outer seal 106 causes plasma 302 to be extruded back into the sample receiving cavity 102 and tapered region 103. Density gel may be combined with any of the embodiments of the cartridge listed herein, with the advantage that the efficiency of plasma recovery (i.e. the percentage of recoverable plasma 302 in the receiving cavity 102) may be increased from mechanical separation alone. The separator gel 1401 may be stably retained in the separation channel 104 due to interfacial tension.

Figure 15A:
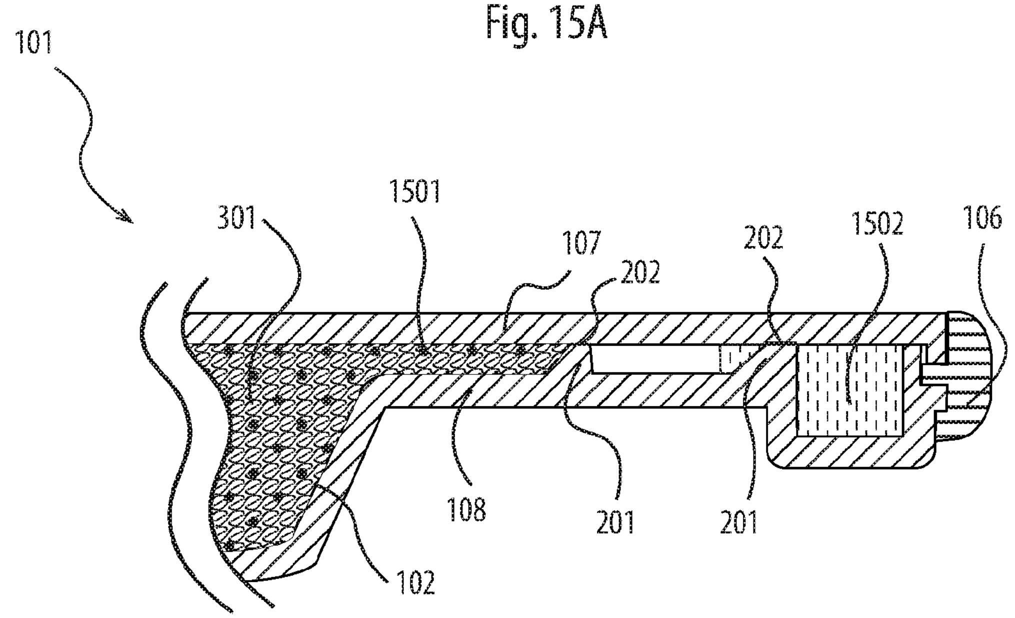
FIGS. 15A-C show a disk-shaped cartridge with a density medium for particle sub-population separation before, during, and after a rotational spin.

Referring now to FIG. 15A, a cross-section side view of a portion of a cartridge embodiment prior to a rotational spin is shown containing a density medium 1502 and a sample fluid 301 containing suspended target particles 1501 such as leukocytes. The cartridge embodiment shown is structurally similar to that described in association with FIG. 2, comprising projections 201 and contact points 202 that may form hermetic seals when the cartridge is at rest. The density medium 1502 may be an aqueous medium with a mass density greater than whole blood or sample fluid 301, and greater than a target particle 1501 such as leukocytes, but less than the density of non-target particles such as red blood cells. The density medium 1502 may comprise silica nanoparticles such as in Percoll or an aqueous solution of high-density salts and polymers such as in Ficoll-Paque. The density medium 1502 may be initially contained in the distal cavity 105. The density medium 1502 may be initially contained in part in annular separation channel 104 and in part in the distal cavity 105. The target particles 1501 may include but not limited to exosomes or circulating tumor cells. Additionally, for exosomes as target particles, the whole blood may be replaced by any sample fluid suspension containing target particles but negligible quantities of cells or platelets. In such application, the acceptable range of plasma residual cell count (i.e., quantities of cells or platelets that may be considered as negligible) may be equal to, or less than 1-0.001% of cell count in the whole blood sample $10^4$-$10^8$ per milliliters.

Figure 15B:
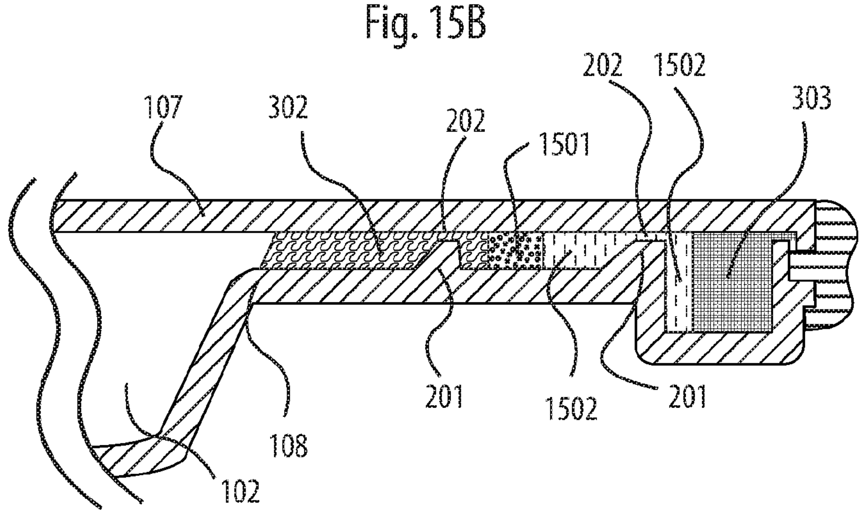

FIG. 15B shows the embodiment of FIG. 15A during a rotational spin. Target particles 1501 may form a layer at the interface between the light fraction represented as plasma 302 and the density medium 1502. Denser non-target particles represented as red blood cells 303 may pass through the density medium 1502 during spin under centrifugal force and may deposit in the distal cavity 105.

Figure 15C:
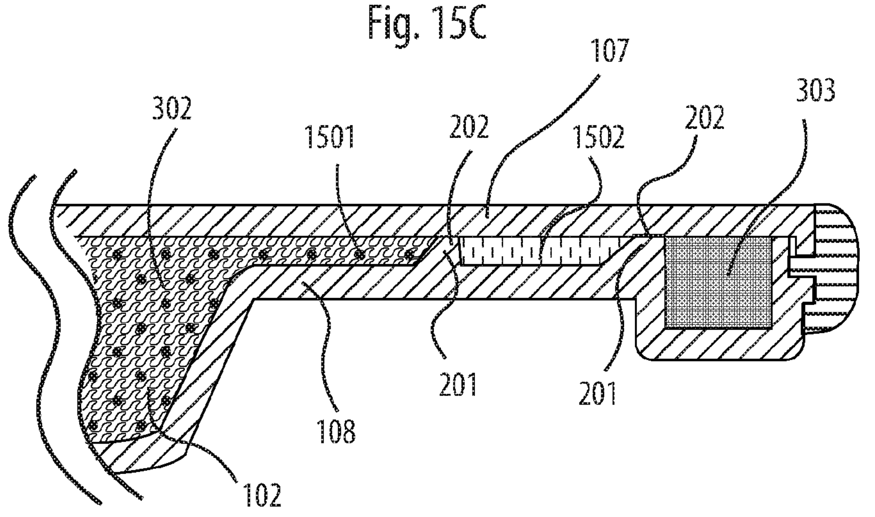

FIG. 15C shows this embodiment of FIG. 15A, after the rotational spin is complete and the cartridge is at rest. Target particles represented as leukocytes 1501 along with blood plasma 302 may be extruded into the sample receiving cavity 102 as the elastic outer seal 106 returns to its initial configuration. In this embodiment, leukocytes and plasma are partitioned from the distal cavity 105 by the annular projections 201. In this embodiment, the density medium 1502 is trapped between two projections 201, which may form hermetic seals at the contact points 202. Alternately, the density medium 1502 may become partially mixed with the plasma fraction 302, which may be acceptable for some uses. The leukocytes 1501 (or other target particles) may then be recovered from the sample receiving cavity 102 without contamination from the red blood cell fraction 303.

Figure 16:
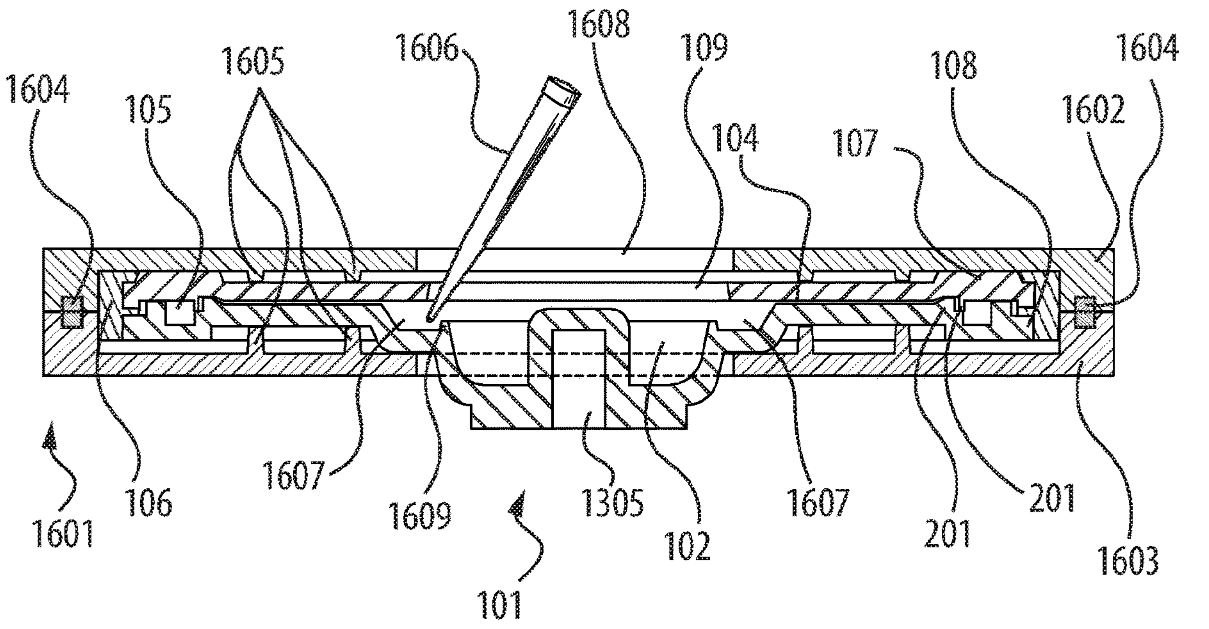
FIG. 16 shows a cross-section of an embodiment comprising a disk-shaped cartridge with plasma collection groove enclosed within a cartridge carrier.

FIG. 16 shows an embodiment of the cartridge 101 that comprises a sample receiving cavity 102, an annular separation channel 104, an inlet hole 109, an annular projection 201, and a hub 1305 for fixing the cartridge on a centrifuge as described earlier. Additionally, in this embodiment, the cartridge 101 may further comprise a plasma collection groove 1607 positioned between the sample receiving cavity 102 and the annular separation channel 104 as a modification to the tapered region mentioned elsewhere. The plasma collection groove 1607 may comprise a cavity between the top plate 107 and the bottom plate 108 and adjacent to the separation channel 104. The plasma collection groove may be bordered by an inner rim 1609 to facilitate capillary retention of plasma. As shown, the inner rim 1609 is an annular rib interior to the cavity of the plasma collection groove 1607. The height of the plasma collection groove 1607 may be greater than the separation channel 104 and less than or equal to the height of the sample receiving cavity 102. The volume of the plasma collection groove 1607 may be equal to or greater than the expected volume of separated plasma following use of the cartridge. For instance, the plasma collection groove 1607 may have a volume between 40% and 100% of the distal cavity 105. The plasma collection groove may be most advantageous when the cartridge is configured for separating small blood volumes such as less than 1 mL blood volume.

Remaining on FIG. 16, the cartridge 101 may be placed within a cartridge carrier 1601 after centrifugation and separation of a sample fluid into its light and heavy fractions such as a plasma fraction and a cellular fraction. The cartridge carrier may comprise a top part 1602, a bottom part 1603 and a means for closure 1604. The cartridge carrier 1601 may be configured to apply pressure to the contained cartridge 101. The cartridge carrier 1601 may further comprise pressure ridges 1605 which may be positioned over ring ridges 201 or other features of the cartridge 101 to enhance the mechanical seal between the distal cavity 105 and other cavities within the cartridge 101. The carrier 1601 may have an outer opening 1608 positioned over the inlet hole 109. An outer opening 1608 may provide access to plasma collection groove 1607 for fluid withdrawal device 1606. The cartridge carrier 1601 may contact with and compress the elastomeric material of the outer seal 106 to form a hermetic outer seal. The cartridge carrier 1601 may provide an extra layer of protection and enhanced mechanical seal between the separated components during storage and shipping. One advantage of using a cartridge carrier 1601 may be improved biosafety such as when transporting separated blood. A cartridge carrier as shown in this figure may be combined with any of the embodiments discussed in association with FIGS. 1A-15C to enhance stability of separation between different fractions of a sample fluid.

Figure 17A:
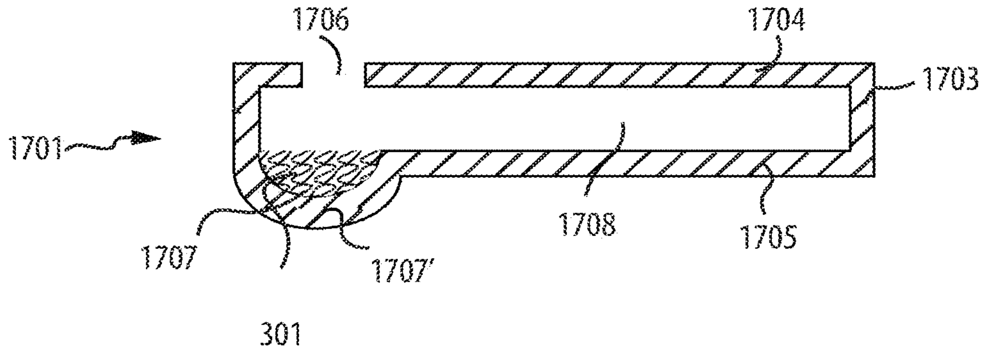
FIGS. 17A-C show a side cross-sectional view of an alternative non-disk shaped embodiment of a cartridge with blood in the entry cavity before, during, and after a rotational spin.

FIG. 17 shows simplified cross-section side views of an embodiment of a non-disk shaped cartridge 1701 in different stages (17A through 17C). FIG. 17A shows the cartridge 1701 loaded with whole blood or sample fluid 301 before the spin. The cartridge 1701 comprises a top plate 1704 affixed to a bottom plate 1705. The top plate 1704 and bottom plate 1705 may be manufactured by injection molding. The top plate 1704 and the bottom plates 1705 may be connected and sealed at a distal end 1703. The top plate 1704 and the bottom plates 1705 form a hollow channel 1708. A recess in the bottom plate 1705 at the proximal end may form a sample receiving cavity 1707, also called an entry chamber, which may have an opening at the top. In FIG. 17A, 1707' indicates the base or bottom of the sample receiving cavity 1707 in the bottom plate 1705. Typically, but not necessarily, the volume of the receiving cavity 1707 may be approximately equal to the volume of the channel 1708, so that the sample fluid loaded into the receiving cavity 1707 may move into the channel 1708 during the spin without overfilling it. Some embodiments may have differing volumes of the receiving cavity 1707 and the channel 1708. An opening in the top plate 1704 may form an inlet hole 1706. Whole blood or sample fluid 301 may be loaded into the cartridge through the inlet hole 1706 and into the receiving cavity 1707. The cartridge 1701 may be spun on a centrifuge to separate the sample fluid 301 into a light portion and a heavy portion such as separation into blood plasma 302 and blood cells 303. The effective spin rate for separation of a light portion and a heavy portion may be between 3000 rpm and 12000 rpm. The effective spin time for separation of a light fraction and a heavy fraction may be between 30 and 600 seconds.

Figure 17B:
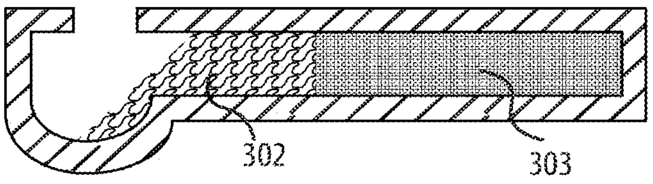
Figure 17C:
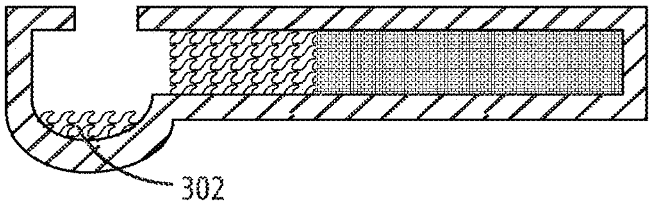

Not shown in FIG. 17A through 17C are attachment elements of a cartridge to a hub or a rotor. Also not shown is an axis of rotation. Referring to FIG. 17A, the axis of rotation would typically be a vertical line left of the sample receiving cavity 1707 perpendicular to the top plate 1704 or at the proximal end of the cartridge 1701.

FIG. 17B shows the embodiment of FIG. 17A during the spin while the blood plasma 302 is separating from blood cells 303. The sample fluid 301 may not fully exit the sample receiving cavity 1707 into the channel 1708 and a portion of the sample fluid may remain in the sample receiving cavity 1707.

FIG. 17C shows the cartridge 1701 after the spin. In FIG. 17B, there may be blood plasma 302 in the receiving cavity 1707 during the spin. This may result some of the blood plasma 302 flowing back into the receiving cavity 1707 after the spin, which may occur as a result of excessive volume of sample fluid 302 loaded into the cartridge. All of the particulate and a portion of the blood plasma 302 may be retained in the channel 1708 due to surface tension and capillary forces.

Figure 18A:
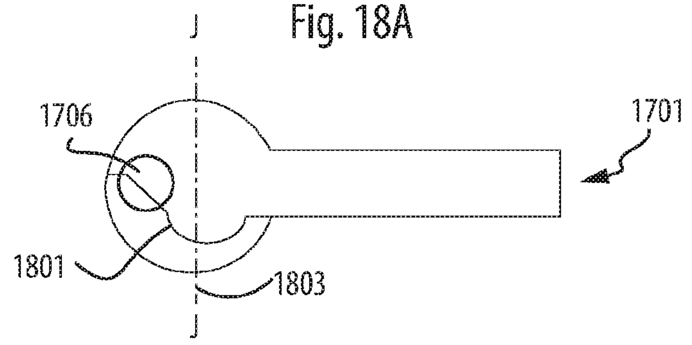
FIGS. 18A-D show top views and cross-sectional side views of embodiments of a cartridge with shallow and deep portions of the sample receiving cavity.
Figure 18B:
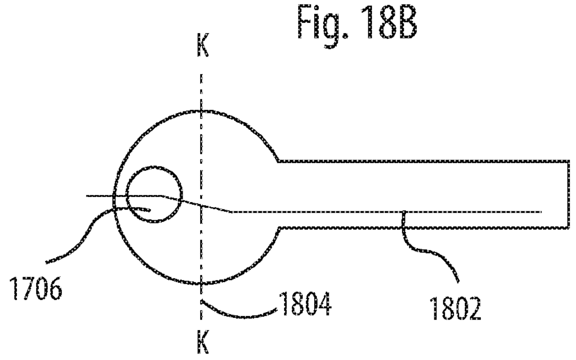
Figure 18C:
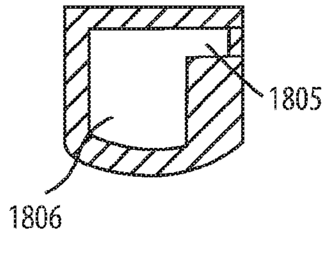
Figure 18D:
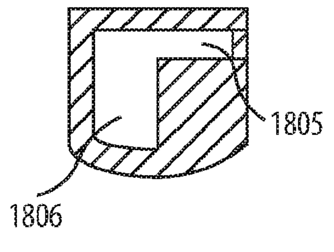

FIG. 18A through 18D show two alternative embodiments. FIGS. 18A and 18B are top views, and FIGS. 18C and 18D are cross-section side views of the embodiments. A cartridge 1701 comprises an inlet hole 1706. A sample receiving cavity 1707 may be constructed with a deep portion and shallow portion as indicated in FIG. 18C by 1806 and 1805, respectively. Line 1801 shows a boundary between the deep and shallow portions in the sample receiving cavity 1707. 1803 shows indicia for cross-section J-J. Due to capillary forces, a sample fluid loaded through inlet hole 1706 may first fill the shallow portion 1805 of the cartridge 1701 with the advantage that air may continue to vent from the inlet hole 1706 as the fluid enters because the inlet 1706 is not surrounded by fluid. The inlet hole 1706 may overlap with both the deep portion 1806 and the shallow portion 1805 to prevent the inlet hole 1706 from being surrounded by fluid.

FIG. 18B shows an alternative embodiment to FIG. 18A. In this embodiment, a shallow portion 1805 of the channel may be shallow and a deep portion 1806 may be deep. The shallow 1805 and deep 1806 portions (see FIG. 18D) may extend from the channel into the sample receiving cavity 1707 as shown in the FIG. 18B. Line 1802 shows a boundary between the deep and shallow portions of the channel. Line 1804 shows indicia for cross-section K-K.

FIG. 18C shows a cross-section J-J from of FIG. 18A. Note a deep portion 1805 and a shallow portion 1806 of the entry cavity.

FIG. 18D shows the cross-section K K through the entry cavity of FIG. 18B. Note a deep portion 1805 and a shallow portion 1806 of the entry cavity.

Figure 19:
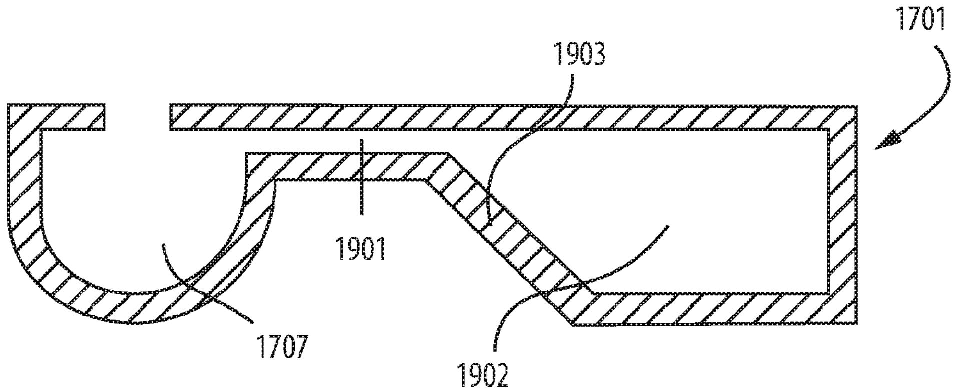
FIG. 19 shows a side cross-sectional view of another embodiment of a cartridge.

FIG. 19 shows a cross-section side view of an alternative embodiment of a cartridge 1701, with a distal cavity 1902, separation channel 1901, and a sample receiving cavity 1707. The channel enlargement may be primarily through a deep channel depth. This embodiment may permit shorter cartridges for the same sample fluid volume.

Figure 20A:
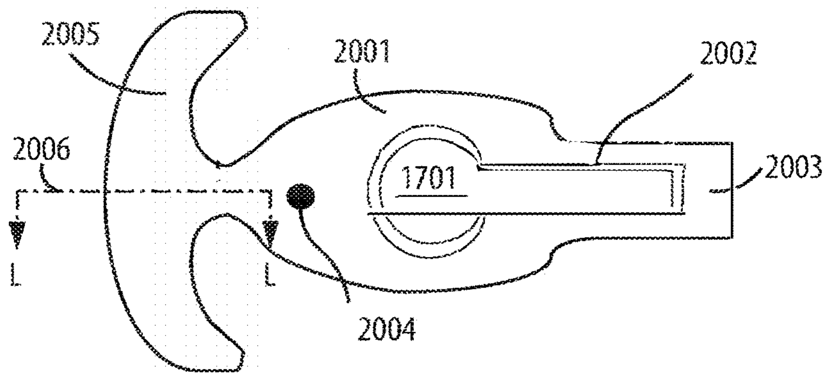
FIGS. 20A-B show a top view and cross-sectional side view of an embodiment comprising a cartridge holder combined with a cartridge.

FIG. 20A shows a top view of yet another embodiment where the cartridge 1701 is reversibly placed into a cartridge holder or carrier 2001. In one embodiment and method of use, the cartridge holder 2001 may be reusable while the cartridges 1701 may be disposable. Additionally, the axis of rotation 2004 may not an embodiment where the cartridge holder 2001 comprises a counterweight 2005. The counterweight is sized so that the center of mass of the cartridge holder 2001 coupled to a fluid-loaded cartridge 1701 is directly over the axis of rotation 2004. 2003 indicates a distal end of the cartridge carrier 1701. Indicia for section L-L is shown by line 2006. The cartridge carrier 2001 may be structured such that the cartridge 1701 is passively retained during centrifugation.

Figure 20B:
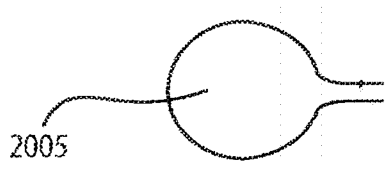

FIG. 20B shows cross-section L-L of the embodiment of FIG. 20A. A round cross-section keeps the counterweight 2005 compact and may also improve aerodynamics of the cartridge holder 2001 during the spin.

Figure 21A:
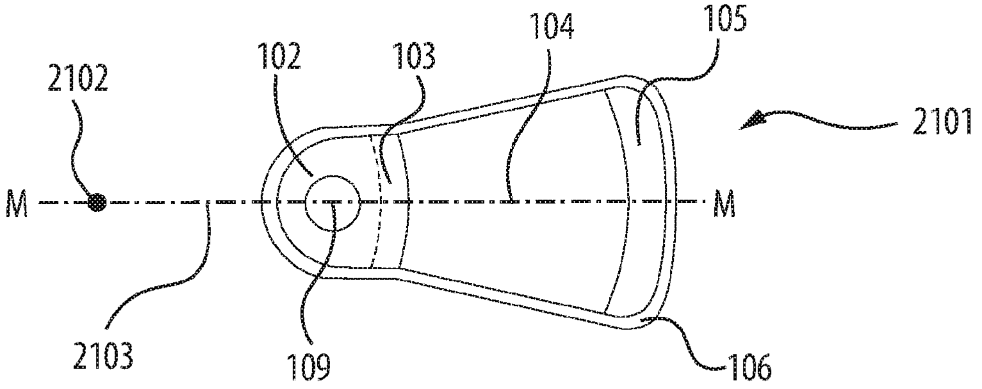
FIGS. 21A-B show a top view and cross-sectional side view of a non-disk shaped cartridge embodiment.

Turning now to FIG. 21A, we show a top view of an embodiment of a non-disk shaped cartridge 2101, which comprises a sample receiving cavity 102, a tapered region outward from the receiving cavity 103, a separation channel 104, a distal cavity 105 outward from the separation channel 104, and an outer seal 106 that secures the top plate 107 and the bottom plate 108. The axis of rotation 2102 would typically be a vertical line left of the sample receiving cavity 102, as shown in FIGS. 21A and 21B.

Figure 21B:
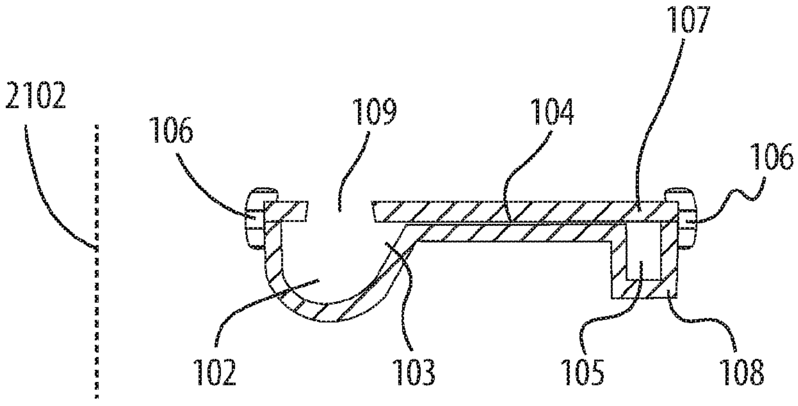

FIG. 21B shows a cross-sectional side view M-M of the embodiment of FIG. 21A as indicated by line 2103. In the embodiment shown, a recess in the bottom plate 108 forms a receiving cavity 102 with a bottom inner surf ace on the bottom plate 108 and a flat top inner surf ace on the top plate 107 and opens at an inlet hole 109 in the top plate. In other embodiments the receiving cavity may be formed from a recess in the top plate only, or a combined recess in the top and bottom plates. The inlet hole 109 is located in fluid communication with the receiving cavity 102 and is positioned, in the embodiment shown, such that a means for fluid withdrawal can access the receiving cavity 102. Outward from the receiving cavity 102, there is a tapered region 103 in fluid communication with the receiving cavity. The combined volume of the receiving cavity 102 and the tapered region 103 will be greater than or equal to the volume of the sample fluid to be received, so that the sample fluid loaded into the receiving cavity 102 may move into the channel 104 during the spin without overfilling it.

A non-disk shaped cartridge similar to 2101 may adopt the elements of disk-shaped embodiments discussed in association with FIGS. 1-9, including an elastomeric outer seal, sample receiving cavity, tapered region, separation channel, and distal cavity. Such a cartridge may have the form of a circular section or wedge shape. In particular, the peripheral detail figures such as FIGS. 2B, 2C, 5A, 5B, 6C, 6D, 6E, 7A, 7B, 7C, and 7D may be translated directly to an elongated cartridge format where the primary features form annular segments rather than a full annulus and where the axis of rotation lies outside of the cartridge proximal to the sample receiving cavity.

Portions of the annular separation channel 104 or channel 1708, such as the 935 interior of the sample receiving cavity 102 or 1707 or the tapered region 103 of the sample receiving cavity 102, may be coated with an initially hydrophobic material such as Scotch Guard® by 3M Company (St. Paul, Mn. 55144-1000). Such a coating may help to avoid a situation where the cartridge is improperly loaded with blood and the inlet hole of the cartridge is surrounded by blood due to the lack of air vent from the inlet hole.

Also, such a coating may also be applied to all surfaces. In addition, such a coating may be applied down a channel, entirely or such as in a radial stripe, to allow air to vent from the channel during spin. Line 1802 in FIG. 18B may be alternatively interpreted to define a line in a channel with a coating on one side only of the line. Such a coating may be converted to have hydrophilic attributes by whole blood. A hydrophilic coating on surface of a separation channel may assist in blood plasma moving to the receiving cavity (102 or 1707) or the plasma collection groove (1607), after spin. A surfactant may be used as a coating. Coatings may comprise an electric charge.

In some embodiments, coatings may be used in the interior of cartridges, such as in the receiving cavity, channels, or other areas or elements. Such coatings may be hydrophobic, hydrophilic, enzymes, dyes, stains, preservatives, thickeners, pH adjustment substances, buffers, proteins, or other substances. In some embodiments, a loose or "floating" element may be introduced that provides a chemical, biological or non-biological substance, such that the chemical will chemically, electrostatically, or mechanically interact with some or all of the fluid(s). Such floating elements may be an alternative to coating an interior portion of the cartridge. In particular, such floating elements may be used if the chemical desired does not have a long shelf life or is not suitable for coating. In some embodiment's microspheres may be used. The diameter of the microspheres may be 0.1 to 500 μm. The microspheres may have a coating such that they may be used to reduce nuclease activity. Microsphere materials may be selected such that they float on top of heavier fluid components, or sink below lighter fluid elements, or are an intermediate density. Microspheres may be used to hold a chemical, such as a coating, or operate as filler.

In one configuration, the embodiment may be used for separation of serum from clotted blood. The cartridge may contain a substance for accelerating clot formation such as silica particles or PDMS-PEO surfactant. A centrifuge device configured to mate with the cartridge may incorporate a means for timing serum generation and a means for mixing blood with a substance for accelerating clot formation. The centrifuge device may facilitate mixing by repeatedly turning the cartridge in one direction and then the other direction. The centrifuge device may spin the cartridge to facilitate serum separation after a time period of between 10 minutes and 60 minutes have passed.

Steps in manufacture of a cartridge may comprise making, by 3D printing, injection molding, stamping, machining, as examples, a top plate and bottom plate; applying any desired coatings and/or filling with density medium or other substance; assembly of the top and bottom plates via ultrasonic welding, adhesive, press-fit, or over-molding; optionally assembly of the top plate and elastic stopper via adhesive, press-fit, or over-molding; placing a removable cover or seal over the inlet hole, or outlet hole, or both; placing a label; and optionally securing a hub. Ideally, the top and bottom plates are monolithic, however there is no such requirement.

An optional, removable cover may be placed over the inlet hole, or outlet hole, or both. The cover may provide cleanliness or sterility for the interior of the cartridge, and may be discarded when removed, replaced after spin, or replaced prior to discarding a used cartridge. Alternatively, a cover may be applied after a fluid is placed into the cartridge to prevent spillage. This cover would be removed prior to removing or extracting separated plasma or other supernatants. The cover may be pierceable, or airtight, or both. A manufactured cartridge may be placed into a sterile bag for shipping or storage. The sterile bag for shipping or storage of manufactured cartridge may be airtight. Cartridges may be serialized or marked, such as with an expiration date.

Steps in use may comprise starting with a cartridge; procuring the cartridge from a shipping or storage bag; removing any seal over the inlet hole or stopper; optionally adding a loose or "floating" element; placing a fluid through the stopper or the inlet hole into the sample receiving cavity; placing an optional removable cover of the inlet hole; placing the cartridge into a centrifuge or into a cartridge carrier; centrifuging the cartridge; removing the cartridge from the centrifuge; and extracting desired plasma or other supernatants, such as by the use of pipette or any means of fluid transfer.

In place of or in addition to extraction of desired plasma, observations or measurements, such as hematocrit, may be made of separated elements in the cartridge. For instance, a centrifuge used with a cartridge may include an imaging system to analyze the height of the blood cell fraction and the height of the plasma fraction near the end of centrifugation in order to estimate hematocrit (the percentage of packed red blood cells by volume) in a blood sample.

A system may comprise a supply of disposable cartridges and a reusable centrifuge. A system may also comprise a reusable cartridge carrier. A system may also comprise tools for use, such as filling or emptying pipettes or cups; components for disposal of used cartridges or waste fluids; and a secondary container for shipping or storage of desired plasma or other supernatants.

Although much discussion herein relates to a cartridge for the isolation or separation of blood plasma from whole blood, sometimes referred to as blood fractionation, there are numerous other biological fluids that may be separated by devices, systems and methods of embodiments. As one example, seminal plasma may be isolated from whole semen. As another example, urine may be separated into lighter and heavier components, such as removing epithelial cells. As yet another example, some biological mixtures start with a collection of non-fluidic cells, such as cell cultures or organ cells, and then the cells are liquefied such as placed in a blender or treated to breakdown cell walls. Embodiments may be used to separate the remaining whole cells. The resulting supernatant may include viruses, proteins, free antibodies, DNA, or other biological elements of interest. In some embodiments a port may provide removal of a centrifugal pellet, which for biological samples, often includes whole cells. In other embodiments, a viewing port in one or both of the top and bottom plate may allow visible inspection of a pellet, media gel, beads and or supernatant. Such inspection may include observation of components, such as particular types of cells, or may include measurements of volume.

Embodiments also include applications for non-biological fluids. In particular, embodiments are appropriate for extracting a lighter fluid from a composition fluid by centrifugal separation of heavier components, such as suspended particles, from the composition fluid. The composition fluid may be a liquid, gas, aerosol, gel, mixture, or suspension. Embodiments described herein, even embodiments with suggested dimensions, volumes, or materials, are non-limiting. Some applications, such as in chemical analysis or assays, pollution control, and chemical manufacturing may use substantially larger components.

Ideal, Ideally, Optimum and Preferred Use of the words, “ideal,” “ideally,” “optimum,” “optimum,” “should” and “preferred,” when used in the context of describing this invention, refer specifically to a best mode for one or more embodiments for one or more applications of this invention. Such best modes are non-limiting, and may not be the best mode for all embodiments, applications, or implementation technologies, as one trained in the art will appreciate.

All examples are sample embodiments. In particular, the phrase “invention” should be interpreted under all conditions to mean, “an embodiment of this invention.” Examples, scenarios, and drawings are non-limiting. The only limitations of this invention are in the claims.

May, Could, Option, Mode, Alternative and Feature Use of the words, “may,” “could,” “option,” “optional,” “mode,” “alternative,” “typical,” “ideal,” and “feature,” when used in the context of describing this invention, refer specifically to various embodiments of this invention. Described benefits refer only to those embodiments that provide that benefit. All descriptions herein are non-limiting, as one trained in the art appreciates. The phrase, “configured to” also means, “adapted to.” The phrase, “a configuration,” means, “an embodiment.”

All numerical ranges in the specification are non-limiting exemplary embodiments only. Brief descriptions of the Figures are non-limiting exemplary embodiments only.

Embodiments of this invention explicitly include all combinations and sub-combinations of all features, elements and limitation of all claims. Embodiments of this invention explicitly include all combinations and sub-combinations of all features, elements, examples, embodiments, tables, values, ranges, and drawings in the specification, Figures, drawings, and all drawing sheets. Embodiments of this invention explicitly include devices and systems to implement any combination of all methods described in the claims, specification and drawings. Embodiments of the methods of invention explicitly include all combinations of dependent method claim steps, in any functional order. Embodiments of the methods of invention explicitly include, when referencing any device claim, a substitution thereof to any and all other device claims, including all combinations of elements in device claims.

We claim:

1. A cartridge configured to receive a sample fluid, wherein the sample fluid comprises a heavy fraction and a light fraction, wherein the cartridge comprises:

a top plate comprising an inlet hole;

a bottom plate;

an outer seal, wherein the outer seal extends along a peripheral edge of the cartridge defined by the top plate and the bottom plate and further extends at least partially between the top plate and the bottom plate, and wherein the outer seal comprises an elastomeric material;

an axis of rotation substantially normal to a horizontal cartridge plane defined by an upper surface of the bottom plate when the cartridge is at rest, wherein the cartridge is configured to rotate about the axis of rotation at an effective rate for centrifugal separation of the heavy fraction from the light fraction;

a sample receiving cavity defined between the top plate and the bottom plate, wherein the sample receiving cavity is fluidly connected to the inlet hole in the top plate, wherein the sample receiving cavity comprises a tapered boundary defining a narrower portion of the sample receiving cavity proximal to the axis of rotation and a wider portion of the sample receiving cavity distal to the axis of rotation;

a distal cavity between the top plate and the bottom plate;

a separation channel defined between the top plate and the bottom plate, the separation channel extending outward from the sample receiving cavity to the distal cavity, wherein the separation channel comprises a top surface and a bottom surface, and, wherein, during rotation of the cartridge, the separation channel is configured to enlarge wherein the separation channel is between the distal cavity and the axis of rotation, wherein the outer seal is configured to expand during rotation of the cartridge, and wherein expansion of the outer seal increases a distance between the top plate and the bottom plate and such that the distal cavity is fluidly connected with the separation channel, wherein a volume of the distal cavity is less than a volume of the sample receiving cavity.

2. The cartridge of claim 1, wherein the cartridge is disk-shaped, and wherein the axis of rotation is within a circumference of the cartridge.

3. The cartridge of claim 1, wherein the sample receiving cavity is centered on the axis of rotation.

4. The cartridge of claim 1, wherein the cartridge comprises a longitudinal axis and a perpendicular cross axis, wherein the longitudinal axis and the perpendicular cross axis lie within the horizontal cartridge plane; wherein the longitudinal wherein the axis of rotation is outside the periphery of the cartridge.

5. The cartridge of claim 1, wherein, at rest, a hermetic seal separates the distal cavity from the sample receiving cavity.

6. The cartridge of claim 1, wherein the top surface of the separation channel and the bottom surface of the separation channel remain substantially parallel during rotation of the cartridge and when the cartridge contains the sample fluid.

7. The cartridge of claim 1, wherein, at rest, the top plate and the bottom plate are in contact with each other within the separation channel.

8. The cartridge of claim 1, wherein the elastomeric material of the outer seal is more flexible than a predominant material of the top plate or the bottom plate.

9. The cartridge of claim 8, wherein the elastomeric material of the outer seal comprises a thermoplastic elastomer and wherein the top plate and the bottom plate comprise a non-elastomeric thermoplastic.

10. The cartridge of claim 1, further comprising an elastomeric stopper, wherein the elastomeric stopper is positionable within the inlet hole of the top plate.

11. A system comprising the cartridge of claim 1 and a gas-impermeable pouch, wherein the cartridge is contained within the gas-impermeable pouch prior to use.

12. The cartridge of claim 1, wherein the cartridge further comprises at least one additional hole radially outward from the inlet hole relative to the axis of rotation, and wherein the at least one additional hole is covered with a pierceable seal.

13. The cartridge of claim 1, further comprising an inner seal between the top plate and the bottom plate, wherein the inner seal is in contact with both the top plate and the bottom plate when the cartridge is at rest.

14. The cartridge of claim 13, wherein the inner seal is configured to form a hermetic seal between the distal cavity and the sample receiving cavity, wherein a fluid passage is defined around the inner seal during rotation of the cartridge and when the cartridge contains the sample fluid.

15. The cartridge of claim 1, wherein the cartridge further comprises at least one projection extending into the separation channel, wherein the at least one projection extends from the bottom surface or the top surface of the separation channel, and wherein, at rest, the at least one projection is configured to span the distance between the top plate and the bottom plate, and wherein a side of the at least one projection facing the axis of rotation is sloped.

16. The cartridge of claim 1, further comprising an inner seal fused to at least one of the top surface or the bottom surface of the separation channel, and wherein the inner seal is configured to form a hermetic seal when the cartridge is at rest.

17. The cartridge of claim 1, further comprising a valve or flap fused to the top surface or the bottom surface of the separation channel, wherein the valve or flap is configured to form a hermetic seal when the cartridge is at rest.

18. The cartridge of claim 17, wherein the valve or flap comprises a first sloped surface on a radially inward side and a second sloped surface on a radially outward side, wherein a curvature of the first sloped surface is different from a curvature of the second sloped surface.

19. The cartridge of claim 1, wherein the cartridge further comprises:

at least one radial groove within the separation channel.

20. The cartridge of claim 19, wherein the at least radial groove extends from the sample cavity to the distal cavity.

21. The cartridge of claim 19, further comprising:

an annular groove within the separation channel.

22. The cartridge of claim 1, further comprising:

a plasma collection cavity having a height taller than a mean height of the separation channel and shorter than a mean height of the distal cavity.

23. The cartridge of claim 1, wherein the sample fluid is whole blood and the light fraction is blood plasma.

24. The cartridge of claim 1, further comprising an anticoagulant between the top plate and the bottom plate.

25. The cartridge of claim 1, further comprising a chemical stabilizer between the top plate and the bottom plate.

26. The cartridge of claim 1, further comprising a separator gel between the top plate and the bottom plate.

27. A method of obtaining a light fraction from a sample fluid comprising the steps: placing the sample fluid into the cartridge of claim 1; connecting the cartridge to a centrifuge; rotating the cartridge at the effective rate for an effective time such that at least a portion of the heavy fraction is contained within the distal cavity after the effective time; allowing the cartridge to come to rest; and withdrawing the light fraction from the sample receiving cavity or tapered region.

28. The method of claim 27, comprising the additional step:

adding the sample fluid with a preservative or anticoagulant.

29. The method of claim 28, wherein the preservative or anticoagulant is effective at reducing nuclease activity.

30. The method of claim 27, wherein: the sample fluid is blood; and comprising the additional step: layering the blood on an aqueous density medium.

31. The method of claim 30, wherein the light fraction comprises leukocytes.

32. The method of claim 27, wherein:

the light fraction comprises exosomes; and the light fraction comprises negligible quantities of cells or platelets.

33. The method of claim 27, wherein the sample fluid comprises a fluid volume of less than one ml.

34. The method of claim 27, wherein the effective rate is between 3000 and 12000 RPM.

35. The method of claim 27, comprising the additional step:

rotating slowly the cartridge at a reduced rate for a second time period different from the effective time period, wherein the reduced rate is slower than the effective rate, and wherein the rotating slowly step is between the rotating and allowing steps.

36. The method of claim 35, wherein the reduced rate is in a range of 1000 to 5000 RPM and the second time period is in a range of 10 to 120 seconds.

37. The method of claim 27, comprising the additional step:

waiting at least 6 hours, wherein the waiting step is between the allowing and withdrawing steps.

38. The method of claim 27, comprising the additional step: waiting at least 20 hours, wherein the waiting step is between the allowing and withdrawing steps.

39. The method of claim 27, comprising the additional step:

waiting at least 48 hours, wherein the waiting step is between the allowing and withdrawing steps.

40. A method of estimating hematocrit of a blood sample comprising:

placing the blood sample into the cartridge of claim 1;

rotating the cartridge at the effective rate capturing an image of the cartridge while rotating at the effective rate;

identifying a plasma fraction and a cellular fraction by optical characteristics of the fractions;

measuring a relative radial length of the plasma fraction to the cellular fraction; and computing a relative volume of the plasma fraction to the cellular fraction.

* * * * *